(12) United States Patent
Mohanty et al.

(10) Patent No.: US 11,890,230 B2
(45) Date of Patent: Feb. 6, 2024

(54) THREE-DIMENSIONAL IMAGE GUIDED SCANNING IRRADIATION DEVICE FOR TARGETED ABLATION, STIMULATION, MANIPULATION, MOLECULAR DELIVERY AND PHYSIOLOGICAL MONITORING

(71) Applicant: Nanoscope Technologies, LLC, Bedford, TX (US)

(72) Inventors: Samarendra Mohanty, Southlake, TX (US); Sanghoon Kim, Euless, TX (US); Subrata Batabyal, Arlington, TX (US); Michael Carlson, Dallas, TX (US)

(73) Assignee: Nanoscope Technologies, LLC, Bedford, TX (US)

( * ) Notice: Subject to any disclaimer, the term of this patent is extended or adjusted under 35 U.S.C. 154(b) by 686 days.

(21) Appl. No.: 17/114,126

(22) Filed: Dec. 7, 2020

(65) Prior Publication Data

US 2021/0177649 A1  Jun. 17, 2021

Related U.S. Application Data

(63) Continuation-in-part of application No. 16/074,041, filed on Jul. 30, 2018, now Pat. No. 10,857,238.
(Continued)

(51) Int. Cl.
*A61N 5/06* (2006.01)
*A61F 9/008* (2006.01)
(Continued)

(52) U.S. Cl.
CPC ............. *A61F 9/008* (2013.01); *A61N 5/062* (2013.01); *A61N 5/067* (2021.08); *A61B 3/102* (2013.01);
(Continued)

(58) Field of Classification Search
CPC .......... A61B 2017/00154; A61B 2018/00428; A61B 2018/00434; A61B 2018/00589;
(Continued)

(56) References Cited

U.S. PATENT DOCUMENTS 6,803,994 B2   10/2004  Margeson
2007/0252951 A1*  11/2007  Hammer ................ A61B 3/103
351/221
(Continued)

FOREIGN PATENT DOCUMENTS

CN    203089533 U   7/2013
CN    103501689 B   6/2016
(Continued)

OTHER PUBLICATIONS

International Search Report PCT/US2017/017636.
(Continued)

*Primary Examiner* — George Manuel
(74) *Attorney, Agent, or Firm* — Shirley A. Recipon

(57) ABSTRACT

The present invention generally relates to an image-guided laser irradiation device for targeted ablation, stimulation, molecular delivery and therapy. Specifically, the invention relates to application of the device in therapies needing precise and targeted removal of a sample, or delivery of impermeable molecules for therapeutic outcome. More specifically, the invention relates to the application of the device in the therapy of visual disorders.

21 Claims, 11 Drawing Sheets

Related U.S. Application Data

(60) Provisional application No. 62/295,030, filed on Feb. 13, 2016.

(51) Int. Cl.

| | |
|---|---|
| *A61N 5/067* | (2006.01) |
| *A61B 18/20* | (2006.01) |
| *A61B 18/00* | (2006.01) |
| *A61B 17/00* | (2006.01) |
| *A61M 37/00* | (2006.01) |
| *A61B 3/135* | (2006.01) |
| *A61B 3/10* | (2006.01) |

(52) U.S. Cl.
CPC ..... *A61B 3/135* (2013.01); *A61B 2017/00154* (2013.01); *A61B 2018/00428* (2013.01); *A61B 2018/00791* (2013.01); *A61B 2018/20553* (2017.05); *A61F 2009/00851* (2013.01); *A61F 2009/00863* (2013.01); *A61F 2009/00891* (2013.01); *A61M 2037/0007* (2013.01); *A61N 2005/0662* (2013.01)

(58) Field of Classification Search
CPC ........... A61B 2018/00791; A61B 2018/20553; A61B 3/102; A61B 3/135; A61F 2009/00851; A61F 2009/00863; A61F 2009/00891; A61F 9/008; A61F 9/00821; A61M 2037/0007; A61N 2005/0662; A61N 5/062; A61N 5/067
See application file for complete search history.

(56) References Cited

U.S. PATENT DOCUMENTS

| | | | |
|---|---|---|---|
| 2011/0111002 A1 | 5/2011 | Pop | |
| 2014/0012224 A1 | 1/2014 | Zhang et al. | |
| 2015/0124219 A1 | 5/2015 | Horn et al. | |
| 2015/0348287 A1* | 12/2015 | Yi ........................ | A61B 5/0073 382/131 |

FOREIGN PATENT DOCUMENTS

| | | |
|---|---|---|
| JP | 2009149593 A | 7/2009 |
| WO | 2014036194 A1 | 3/2014 |
| WO | 2014066598 A1 | 5/2014 |
| WO | 2014158263 A1 | 10/2014 |
| WO | 2015157761 A1 | 10/2015 |

OTHER PUBLICATIONS

International Search Report PCT/US2017/017636 dated Apr. 25, 2017.
Ishikawa Y, Mine S. Aminoadipic Acid Toxic Effects on Retinal Glial-Cells. Jpn J Ophthalmol. 1983; 27(1):107-18.
Ivanova E, Roberts R, Bissig D, Pan Z-H, Berkowitz B A. Retinal channelrhodopsin-2-mediated activity in vivo evaluated with manganese-enhanced magnetic resonance imaging. J Molecular Vision. 2010; 16:1059-67.
Jacobson S G, Roman A J, Aleman T S, Sumaroka A, Herrera W, Windsor E A, et al. Normal central retinal function and structure preserved in retinitis pigmentosa. Invest Ophthalmol Vis Sci. 2010; 51(2):1079-85.
Johansen J P, Hamanaka H, Monfils M H, Behnia R, Deisseroth K, Blair H T, et al. Optical activation of lateral amygdala pyramidal cells instructs associative fear learning. Proc Natl Acad Sci. 2010; 107(28):12692-7.
JP Office Action Summary, dated Sep. 5, 2019.
Kam, N.W.S., et al.; "Carbon nanotubes as multifunctional biological transporters and near-infrared agents for selective cancer cell destruction," Proceedings of the National Academy of Sciences, vol. 102, No. 33, pp. 11600-11605 (Aug. 16, 2005).
Kamimura K, Suda T, Zhang G, Liu D. Advances in Gene Delivery Systems. Pharmaceut. Med. 2011; 25(5):293-306.
Kavalali E T, Jorgensen E M. Visualizing presynaptic function. Nat Neurosci. 2014; 17(1):10-6.
Kim B, Han G, Toley B J, Kim C-k, Rotello V M, Forbes N S. Tuning payload delivery in tumour cylindroids using gold nanoparticles. Nat Nano. 2010; 5(6):465-72.
King R. Gene Delivery to Mammalian Cells by Microinjection. Methods in Molecular Biology. 2004; 245(2):167-73.
Klein M L, Ferris F L, 3rd, Francis P J, Lindblad A S, Chew E Y, Hamon S C, et al. Progression of geographic atrophy and genotype in age-related macular degeneration. Ophthalmology. 2010; 117(8):1554-9, 9 e1.
Koizumi A, Tanaka K F, Yamanaka A. The manipulation of neural and cellular activities by ectopic expression of melanopsin. Neurosci Res. 2013; 75(1):3-5.
Kraszewski K, Mundigl O, Daniell L, Verderio C, Matteoli M, De Camilli P. Synaptic vesicle dynamics in living cultured hippocampal neurons visualized with CY3-conjugated antibodies directed against the lumenal domain of synaptotagmin. J Neurosci. 1995; 15(6):4328-42.
Lagali P S, Balya D, Awatramani G B, Munch T A, Kim D S, Busskamp V, et al. Light-activated channels targeted to ON bipolar cells restore visual function in retinal degeneration. Nat Neurosci. 2008; 11(6):667-75.
Li S, Huang L. Nonviral gene therapy: promises and challenges. Gene Ther. 2000; 7(1):31-4.
Li Z Y, Jacobson S G, Milam A H. Autosomal dominant retinitis pigmentosa caused by the threonine-17-methionine rhodopsin mutation: retinal histopathology and immunocytochemistry. Exp Eye Res. 1994; 58(4):397-408.
Liao, Hongwei, et al.; "Biomedical applicaitons of plasmon resonant metal nanoparticles," Nanomedicine (2006) 1(2), 201-208; Aug. 1, 2006.
Luo D, Saltzman W M. Synthetic DNA delivery systems. Nat Biotech. 2000; 18(1):33-7.
Melancon, Marites P., et al.; "Cancer Theranostics with Near-Infrared Light-Activatable Multimodal Nanoparticles," Accounts of Chemical Research, vol. 44, No. 10,pp. 947-956; Oct. 18, 2011.
Mezer E, Babul-Hirji R, Wise R, Chipman M, DaSilva L, Rowell M, et al. Attitudes Regarding Predictive Testing for Retinitis Pigmentosa. Ophthalmic Genetics. 2007; 28(1):9-15.
Miller G. Shining New Light on Neural Circuits. Science. 2006; 314(5806):1674-6.
Mohanty S K, Reinscheid R K, Liu X, Okamura N, Krasieva T B, Berns M W. In-Depth Activation of Channelrhodopsin 2-Sensitized Excitable Cells with High Spatial Resolution Using Two-Photon Excitation with a Near-Infrared Laser Microbeam. Biophys J. 2008; 95(8):3916-26.
Mohanty S K, Sharma M, Gupta P K. Laser-assisted microinjection into targeted animal cells. Biotech Lett. 2003; 25 (11):895-9.
Nagel G, Brauner M, Liewald J F, Adeishvili N, Bamberg E, Gottschalk A. Light activation of channelrhodopsin-2 in excitable cells of Caenorhabditis elegans triggers rapid behavioral responses. Curr Biol. 2005; 15(24):2279-84.
Nagel G, Szellas T, Huhn W, Kateriya S, Adeishvili N, Berthold P, et al. Channelrhodopsin-2, a directly light-gated cation-selective membrane channel. Proc Nat Acad Sci. 2003; 100(24):13940-5.
Naldini L, Blomer U, Gallay P, Ory D, Mulligan R, Gage F H, et al. In Vivo Gene Delivery and Stable Transduction of Nondividing Cells by a Lentiviral Vector. Science. 1996; 272(5259):263-7.
Newman C M, Lawrie A, Brisken A F, Cumberland D C. Ultrasound Gene Therapy: On the Road from Concept to Reality. Echocardiography. 2001; 18(4):339-47.
Noh, M.S et al., Biomaterials, 2015, vol. 45, p. 81-92.
Office Action, EP17750949.4, dated Mar. 2021.
Office Action, May 2020, JP2018-543151.
Palumbo G, Caruso M, Crescenzi E, Tecce M F, Roberti G, Colasanti A. Targeted gene transfer in eucaryotic cells by dye-assisted laser optoporation. J Photochem Photobiol B. 1996; 36(1):41-6.

(56) References Cited

OTHER PUBLICATIONS

Panyam J, Labhasetwar V. Biodegradable nanoparticles for drug and gene delivery to cells and tissue. Adv Drug Deliv Rev. 2003; 55(3):329-47.

Pastrana E. Optogenetics: controlling cell function with light. Nat Meth. 2011; 8(1):24-5.

Pedersen O O, Karlsen R L. Destruction of Muller cells in the adult rat by intravitreal injection of D,L-alpha-aminoadipic acid. An electron microscopic study. Exp Eye Res. 1979; 28(5):569-75.

Ruitenberg M J, Eggers R, Boer G J, Verhaagen J. Adeno-associated viral vectors as agents for gene delivery: application in disorders and trauma of the central nervous system. Methods. 2002; 28(2):182-94.

Sahaboglu A, Paquet-Durand O, Dietter J, Dengler K, Bernhard-Kurz S, Ekstrom P A, et al.; Retinitis pigmentosa: rapid neurodegeneration is governed by slow cell death mechanisms. Cell Death Dis. 2013; 4:e488.

Schinkel H, Jacobs P, Schillberg S, Wehner M. Infrared picosecond laser for perforation of single plant cells. Biotechnol Bioeng. 2008; 99(1):244-8.

Schneckenburger H, Hendinger A, Sailer R, Strauss W S, Schmitt M. Laser-assisted optoporation of single cells. J Biomed Opt. 2002; 7(3):410-6.

Schomaker, M., et al. (2015) "Characterization of nanoparticle mediated laser transfection by femtosecond laser pulses for applications in molecular medicine." Journal of nanobiotechnology, vol. 13, No. 10.

Schomaker, M., et al.(2010) "Fs-laser cell perforation using gold nanoparticles of different shapes." Frontiers in Ultrafast Optics: Biomedical, Scientific, and Industrial Applications X. Vol. 7589, pp. 75890C-1-5.

Schomaker, Markus, et al.; "Characterization of nanoparticle mediated laser transfection by femtosecond laser pulses for applications in molecular medicine," Journal of Nanobiotechnology (2015) 13:10; Feb. 3, 2015.

Schroll C, Riemensperger T, Bucher D, Ehmer J, Voller T, Erbguth K, et al. Light-induced activation of distinct modulatory neurons triggers appetitive or aversive learning in *Drosophila larvae*. Current Biology. 2006; 16(17):1741-7.

Shivalingaiah S, Gu L, Mohanty S K. Correlation of spatial intensity distribution of light reaching the retina and restoration of vision by optogenetic stimulation. Proc SPIE. 2011; 7885:78851Y.

Shivalingaiah S, Gu L, Mohanty S K. Non-linear stimulation of excitable cells with and without optogenetic sensitization. Proc SPIE 2011; 7883:788355.

Somia N, Verma I M. Gene therapy: trials and tribulations. Nat Rev Genet. 2000; 1(2):91-9.

Stracke F, Rieman J, Konig K. Optical nanoinjection of macromolecules into vital cells; Journal of Photochemistry and Photobiology B: Biology. 2005; 81(3):136-42.

Sugano E, Isago H, Wang Z, Murayama N, Tamai M, Tomita H. Immune responses to adeno-associated virus type 2 encoding channelrhodopsin-2 in a genetically blind rat model for gene therapy. Gene Ther. 2011; 18(3):266-74.

Sugawara T, Hagiwara A, Hiramatsu A, Ogata K, Mitamura Y, Yamamoto S. Relationship between peripheral visual field loss and vision-related quality of life in patients with retinitis pigmentosa. Eye (Lond). 2010; 24(4):535-9.

57. Gobin A M, Lee M H, Halas N J, James W D, Drezek R A, West J L. Near-Infrared Resonant Nanoshells for Combined Optical Imaging and Photothermal Cancer Therapy. Nano Letters. 2007; 7(7):1929-34.

Adamantidis A R, Tsai H C, Boutrel B, Zhang F, Stuber G D, Budygin E A, et al. Optogenetic interrogation of dopaminergic modulation of the multiple phases of reward-seeking behavior. J Neurosci. 2011; 31(30):10829-35.

Adijanto, Jeffrey, et al.; "Nanoparticle-based technologies for retinal gene therapy," European Journal of Pharmaceutics and Biopharmaceutics 95 (2015) 353-367 (Jan. 12, 2015).

Akilov O E, Wu M X, Jin Y, Zhou Z, Geskin L J, Falo L D, et al. Vaccination with photodynamic therapy-treated macrophages induces highly suppressive T-regulatory cells. Photodermatol, Photoimmunol Photomed. 2011; 27 (2):97-107.

Alilain W J, Li X, Horn K P, Dhingra R, Dick T E, Herlitze S, et al. Light-Induced Rescue of Breathing after Spinal Cord Injury. J Neurosci. 2008; 28(46):11862-70.

Baumgart, J., et al.; "Plasmonic enhanced fs-laser optoporation of human melanoma cells," Frontiers in Ultrafast Optics: Biomedical, Scientific and Industrial Applications XI, SPIE; Proc. of SPIE vol. 7925 792501-1, pp. 1-6; Feb. 10, 2011.

Baumgartner W A. Etiology, pathogenesis, and experimental treatment of retinitis pigmentosa. Medical Hypotheses. 2000; 54(5):814-24.

Bi A D, Cui J J, Ma Y P, Olshevskaya E, Pu M L, Dizhoor A M, et al. Ectopic expression of a microbial-type rhodopsin restores visual responses in mice with photoreceptor degeneration. Neuron. 2006; 50(1):23-33.

Bi A, Cui J, Ma Y P, Olshevskaya E, Pu M, Dizhoor A M, et al. Ectopic expression of a microbial-type rhodopsin restores visual responses in mice with photoreceptor degeneration. Neuron. 2006; 50(1):23-33.

Biarnes M, Mones J, Alonso J, Arias L. Update on geographic atrophy in age-related macular degeneration. Optom Vis Sci. 2011; 88(7):881-9.

Boyden E S, Zhang F, Bamberg E, Nagel G, Deisseroth K. Millisecond-timescale, genetically targeted optical control of neural activity. Nat Neurosci. 2005; 8(9):1263-8.

Brongersma M L. Nanoscale photonics: Nanoshells: gifts in a gold wrapper. Nat Mater. 2003; 2(5):296-7.

Burridge K, Feramisco J R. Microinjection and localization of a 130K protein in living fibroblasts: a relationship to actin and fibronectin. Cell. 1980; 19(3):587-95.

Busskamp V, Duebel J, Balya D, Fradot M, Viney T J, Siegert S, et al. Genetic Reactivation of Cone Photoreceptors Restores Visual Responses in Retinitis Pigmentosa. Science. 2010; 329(5990):413-7.

Busskamp V, Picaud S, Sahel J A, Roska B. Optogenetic therapy for retinitis pigmentosa; Gene Ther. 2012; 19 (2):169-75.

Cao H, Gu L, Mohanty S K, Chiao J C. An Integrated mu LED Optrode for Optogenetic Stimulation and Electrical Recording. Ieee T Bio-Med Eng. 2013; 60(1):225-9.

Chader G J. Animal models in research on retinal degenerations: past progress and future hope. Vision Res. 2002; 42 (4):393-9.

Charan, S. et al., Bioconjug Chem, 2012, vol. 23, p. 2173-83.

Chatrchyan, S et al.; "The CMS experiment at the Cern LHC," Journal of Instrumentation, Institute of Physics Publishing, vol. 3, No. 8, Aug. 1, 2008.

Chen J, Saeki F, Wiley B J, Cang H, Cobb M J, Li Z-Y, et al. Gold Nanocages: Bioconjugation and Their Potential Use as Optical Imaging Contrast Agents. Nano Letters. 2005; 5(3):473-7.

Chen J, Wang D, Xi J, Au L, Siekkinen A, Warsen A, et al. Immuno Gold Nanocages with Tailored Optical Properties for Targeted Photothermal Destruction of Cancer Cells. Nano Letters. 2007; 7(5):1318-22.

Cheng Y, Samia A C, Li J, Kenney M E, Resnick A, Burda C. Delivery and efficacy of a cancer drug as a function of the bond to the gold nanoparticle surface. Langmuir. 2010; 26(4):2248-55.

CP010-0001AU-U1 Australian office action.

CP010-0001AU-U1 Australian office action dated Dec. 2019.

Curcio C A, Medeiros N E, Millican C L. Photoreceptor loss in age-related macular degeneration. Invest Ophthalmol Vis Sci. 1996; 37(7):1236-49.

Daiger S P, Bowne S J, Sullivan L S. Perspective on genes and mutations causing retinitis pigmentosa. Arch Ophthalmol. 2007; 125(2):151-8.

Deisseroth K. Optogenetics. Nat Meth. 2011; 8(1):26-9.

Dhakal K, Black B, Mohanty S. Introduction of impermeable actin-staining molecules to mammalian cells by optoporation. Sci Rep. 2014; 4(6553):1-7.

Dhakal K, Gu L, Shivalingaiah S, Dennis T, Bobzean S, Perrotti L, et al. Non-scanning fiber-optic near-infrared beam led to two-photon optogenetic stimulation in vivo. Plos One. 2014; in press.

(56) References Cited

OTHER PUBLICATIONS

Dichtl A, Jonas J B, Naumann G O. Retinal nerve fiber layer thickness in human eyes; Graefe's archive for clinical and experimental ophthalmology. 1999; 237(6):474-9.

Doroudchi M M, Greenberg K P, Liu J, Silka K A, Boyden E S, Lockridge J A, et al. Virally delivered Channelrhodopsin-2 Safely and Effectively Restores Visual Function in Multiple Mouse Models of Blindness. Mol Ther. 2011; 19(7):1220-9.

Editorial, Method of the Year 2010. Nat Meth. 2011; 8(1):1-.

European Written Opinion EP17750949.

Fehrentz T, Schonberger M, Trauner D. Optochemical genetics. Angew Chem Int Ed Engl. 2011; 50(51):12156-82.

Fenno L, Yizhar O, Deisseroth K. The Development and Application of Optogenetics. Ann Rev Neurosci. 2011; 34 (1):389-412.

Ferber D. Safer and Virus-Free? Science. 2001; 294(5547):1638-42.

Fernandez de Castro J P, Scott P A, Fransen J W, Demas J, DeMarco P J, Kaplan H J, et al. Cone photoreceptors develop normally in the absence of functional rod photoreceptors in a transgenic swine model of retinitis pigmentosa. Invest Ophthalmol Vis Sci. 2014; 55(4):2460-8.

Flannery J G, Farber D B, Bird A C, Bok D. Degenerative changes in a retina affected with autosomal dominant retinitis pigmentosa. Invest Ophthalmol Vis Sci. 1989; 30(2):191-211.

Fleckenstein M, Schmitz-Valckenberg S, Adrion C, Kramer 1, Eter N, Helb H M, et al. Tracking progression with spectral-domain optical coherence tomography in geographic atrophy caused by age-related macular degeneration. Invest Ophthalmol Vis Sci. 2010; 51(8):3846-52.

Grover S, Fishman G A, Anderson R J, Alexander K R, Derlacki D J. Rate of visual field loss in retinitis pigmentosa. Ophthalmology. 1997; 104(3):460-5.

Grunwald J E, Pistilli M, Ying G S, Maguire M G, Daniel E, Martin D F. Growth of Geographic Atrophy in the Comparison of Age-related Macular Degeneration Treatments Trials. Ophthalmology. 2014.

Gu L, Mohanty S K. Targeted microinjection into cells and retina using optoporation. J Biomed Opt. 2011; 16 (12):128003-6.

Gu, L., et al.; "Crystalline magnetic carbon nanoparticle assisted photothermal delivery into cells using CW near-infrared laser beam," Scientific Reports, No. 4, Article: 5106; May 29, 2014.

Hamel C. Retinitis pigmentosa. Orphanet J Rare Dis. 2006; 1:40.

Han X, Boyden E S. Multiple-Color Optical Activation, Silencing, and Desynchronization of Neural Activity, with Single- Spike Temporal Resolution. PLoS ONE. 2007; 2(3):e299.

Hao, Y. et al., J Control Release, 2015, vol. 220, p. 545-55.

Hartong D T, Berson E L, Dryja T P. Retinitis pigmentosa. Lancet. 2006; 368(9549):1795-809.

Hosokawa Y, Iguchi S, Yasukuni R, Hiraki Y, Shukunami C, Masuhara H. Gene delivery process in a single animal cell after femtosecond laser microinjection. Appl Surf Sci. 2009; 255(24):9880-4.

Huang X, El-Sayed I H, Qian W, El-Sayed M A. Cancer Cell Imaging and Photothermal Therapy in the Near-Infrared Region by Using Gold Nanorods. Journal of the American Chemical Society. 2006; 128(6):2115-20.

Huang, Xiao, et al.; "Light-activated RNA interference in human embryonic stem cells," 63 Biomaterials (2015) 70-79; Jun. 10, 2015.

Sunness J S, Applegate C A, Bressler N M, Hawkins B S. Designing clinical trials for age-related geographic atrophy of the macula: enrollment data from the geographic atrophy natural history study. Retina. 2007; 27(2):204-10.

Sunness J S, Margalit E, Srikumaran D, Applegate C A, Tian Y, Perry D, et al. The long-term natural history of geographic atrophy from age-related macular degeneration: enlargement of atrophy and implications for interventional clinical trials. Ophthalmology. 2007; 114(2):271-7.

Supplemental Partial European Search Report.

Supplementary European Search Report EP17750949.

Tao W, Wilkinson J, Stanbridge E J, Berns M W. Direct gene transfer into human cultured cells facilitated by laser micropuncture of the cell membrane. Proc Natl Acad Sci USA. 1987; 84(12):4180-4.

Templeton N S, Lasic D D, Frederik P M, Strey H H, Roberts D D, Pavlakis G N. Improved DNA: liposome complexes for increased systemic delivery and gene expression. Nat Biotech. 1997; 15(7):647-52.

Thomas C E, Ehrhardt A, Kay M A. Progress and problems with the use of viral vectors for gene therapy. Nat Rev Genet. 2003; 4(5):346-58.

Thyagarajan S, van Wyk M, Lehmann K, Lowel S, Feng G, Wassle H. Visual Function in Mice with Photoreceptor Degeneration and Transgenic Expression of Channelrhodopsin 2 in Ganglion Cells. J Neurosci. 2010; 30(26):8745-58.

Tirlapur U K, Konig K. Femtosecond near-infrared laser pulses as a versatile non-invasive tool for intra-tissue nanoprocessing in plants without compromising viability. Plant J. 2002; 31(3):365-74.

Tirlapur U K, Konig K. Targeted transfection by femtosecond laser. Nature. 2002; 418(6895):290-1.

Tomita H, Sugano E, Fukazawa Y, Isago H, Sugiyama Y, Hiroi T, et al. Visual Properties of Transgenic Rats Harboring the Channelrhodopsin-2 Gene Regulated by the Thy-1.2 Promoter. PLoS One. 2009; 4(11).

Tomita H, Sugano E, Isago H, Hiroi T, Wang Z, Ohta E, et al. Channelrhodopsin-2 gene transduced into retinal ganglion cells restores functional vision in genetically blind rats. Experimental Eye Research. 2010; 90(3):429-36.

Tong L, Zhao Y, Huff T, Hansen M, Wei A, Cheng J X. Gold Nanorods Mediate Tumor Cell Death by Compromising Membrane Integrity. Advanced Materials. 2007; 19(20):3136-41.

Tonnesen J, Parish C L, Sorensen A T, Andersson A, Lundberg C, Deisseroth K, et al.; Functional Integration of Grafted Neural Stem Cell-Derived Dopaminergic Neurons Monitored by Optogenetics in an In Vitro Parkinson Model. PLoS ONE. 2011; 6(3):e17560.

Tsien R Y. The Gree Fluorescent Protein. Ann Rev Biochem. 1998; 67(1):509-44.

Verma I M, Somia N. Gene therapy—promises, problems and prospects. Nature 1997; 389(6648):239-42.

Wallsh J, Gallemore R. Optical coherence tomography difference maps and average macular volume for geographic atrophy. Retin Cases Brief Rep. 2015; 9(1):88-91.

Wang S, Chen K J, Wu TH, Wang H, Lin W Y, Ohashi M, et al. Photothermal Effects of Supramolecularly Assembled Gold Nanoparticles for the Targeted Treatment of Cancer Cells. Angewandte Chemie. 2010; 122(22):3865-9.

Wijaya, Andy, et al.; "Selective Release of Multiple DNA Oligonucleotides from Gold Nanorods," ACS Nano, vol. 3, No. 1, p. 80-86 (Dec. 16, 2008).

Written Opinion of the ISA PCT/US2017/017636.

Wu Z, Ayton L N, Luu C D, Guymer R H. Microperimetry of nascent geographic atrophy in age-related macular degeneration. Invest Ophthalmol Vis Sci. 2015; 56(1):115-21.

Yu J-Y, DeRuiter S L, Turner D L. Rna interference by expression of short-interfering RNAs and hairpin RNAs in mammalian cells. Proc Nat Acad Sci. 2002; 99(9):6047-52.

Zhang F, Aravanis A M, Adamantidis A, de Lecea L, Deisseroth K. Circuit-breakers: optical technologies for probing neural signals and systems. Nat Rev Neurosci. 2007; 8(8):577-81.

Zhang F, Wang L P, Boyden E S, Deisseroth K. Channelrhodopsin-2 and optical control of excitable cells. Nat Methods. 2006; 3(10):785-92.

Zhang Y, Ivanova E, Bi A, Pan Z-H. Ectopic Expression of Multiple Microbial Rhodopsins Restores ON and OFF Light Responses in Retinas with Photoreceptor Degeneration. J Neurosci. 2009; 29(29):9186-96.

Zufferey R, Nagy D, Mandel R J, Naldini L, Trono D. Multiply attenuated lentiviral vector achieves efficient gene delivery in vivo. Nat Biotech. 1997; 15(9):871-5.

JP Office Action Summary, dated Aug. 10, 2021, JP Appl. No. 2020-149423.

(56) References Cited

OTHER PUBLICATIONS

Huschka, Ryan, et al.; "Gene Silencing by Gold Nanoshell-Mediated Delivery and Laser-Triggered Release of Antisense Oligonucleotide and siRNA," ACS Nano, vol. 6, No. 9, Sep. 25, 2012, pp. 7681-7691.
Office Action, CN201780010827.2, dated Jan. 2021.
Wang, Bei-Ke, et al.; "Gold nanorods-siRNA nanoplex for improved photothermal therapy by gene silencing," Biomaterials 78 (2016) 27-39, Nov. 19, 2015.

\* cited by examiner

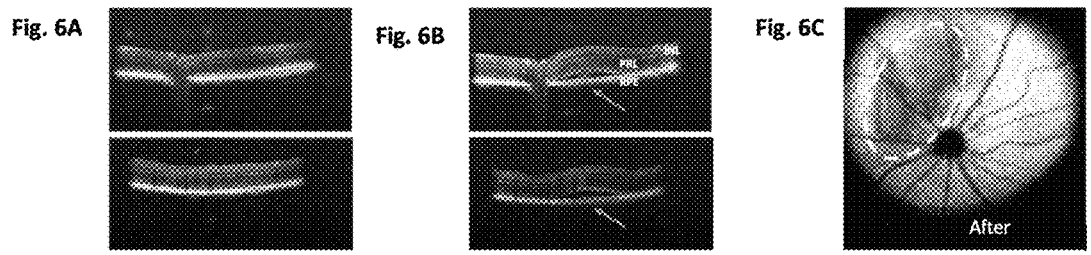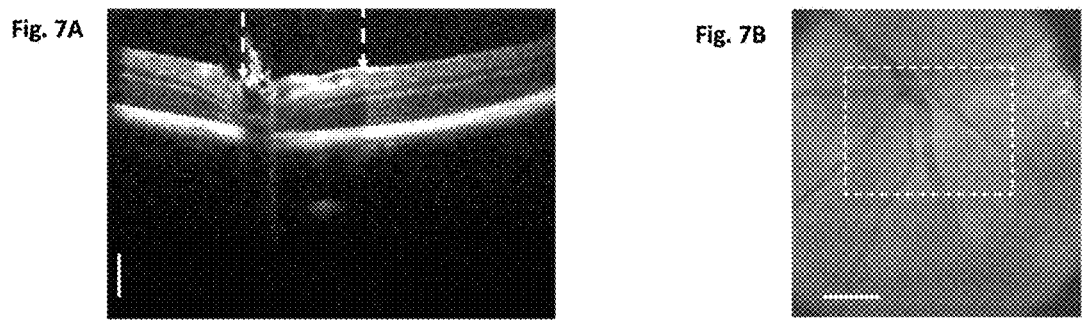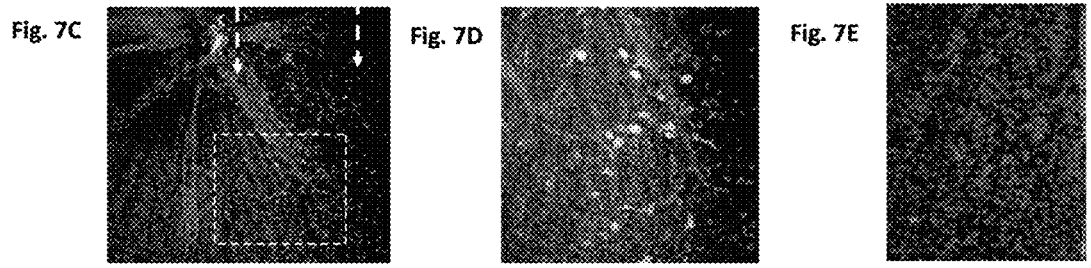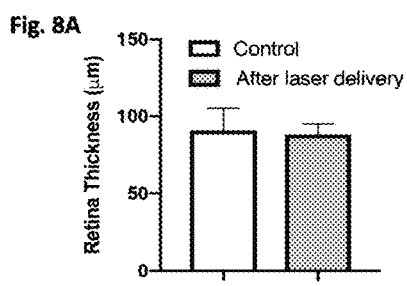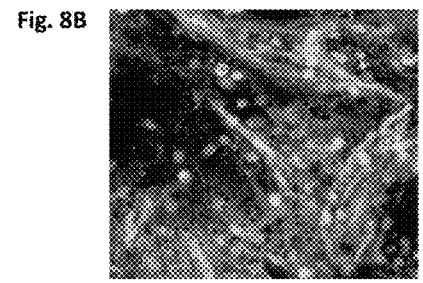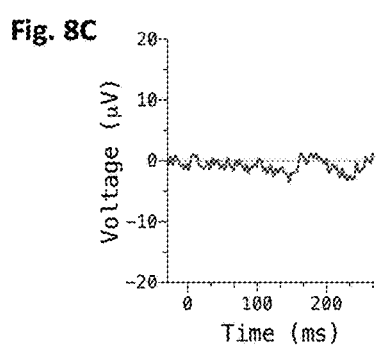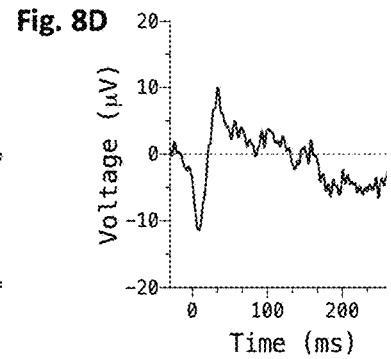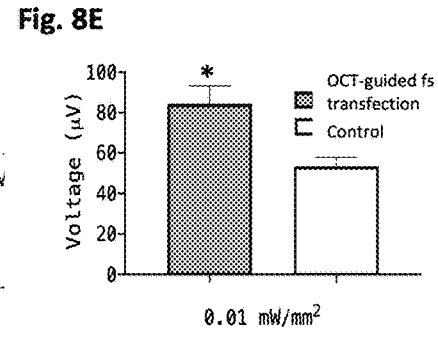

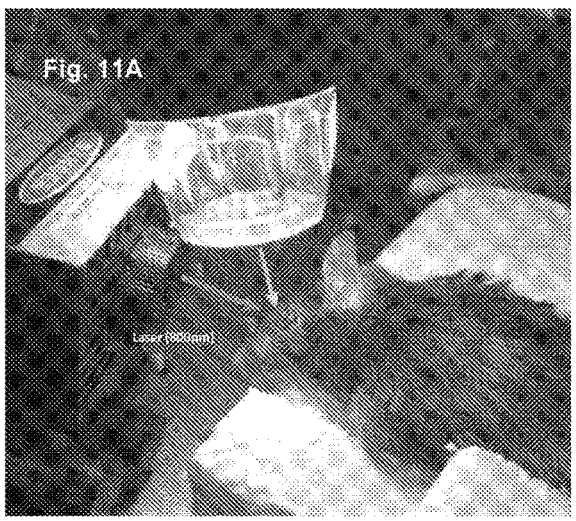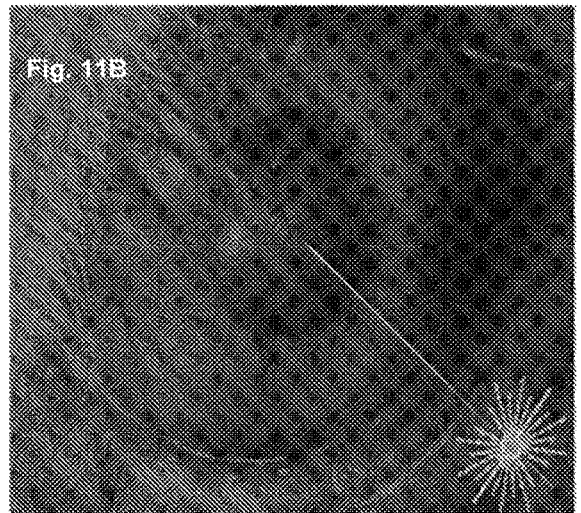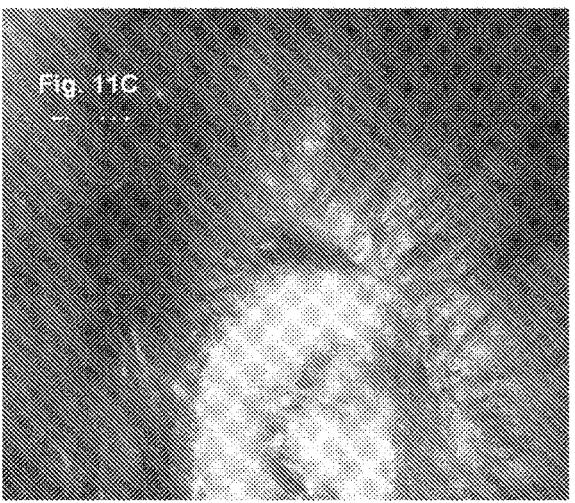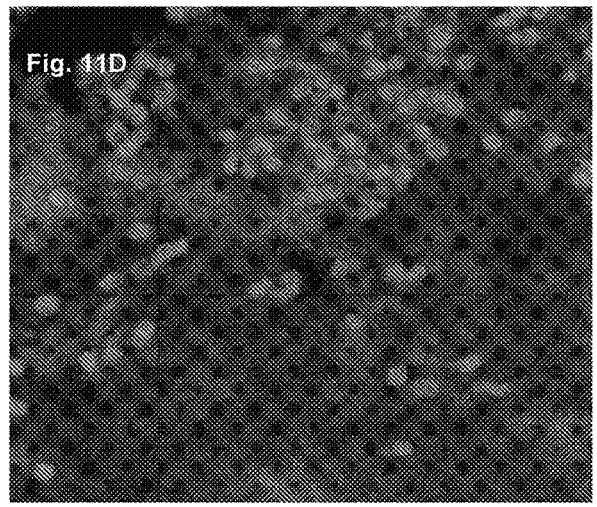

THREE-DIMENSIONAL IMAGE GUIDED SCANNING IRRADIATION DEVICE FOR TARGETED ABLATION, STIMULATION, MANIPULATION, MOLECULAR DELIVERY AND PHYSIOLOGICAL MONITORING

CROSS-REFERENCE TO RELATED APPLICATIONS

This application is a continuation-in-part of U.S. patent application Ser. No. 16/074,041, filed Feb. 13, 2017, which in turn claims the benefit of priority to U.S. provisional application Ser. No. 62/295,030, filed Feb. 13, 2016, all of which are hereby incorporated by reference in their entirety.

CROSS-REFERENCE

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

STATEMENT REGARDING FEDERALLY SPONSORED RESEARCH OR DEVELOPMENT

This invention was made with funding by Nanoscope Technologies, LLC. The Government has no rights in the invention.

FIELD OF INVENTION

The present invention generally relates to an image-guided laser irradiation device for targeted ablation, cell specific damage, stimulation, molecular delivery and therapy. Specifically, the invention relates to application of the device in therapies needing precise and targeted removal of a sample, or delivery of impermeable molecules for a therapeutic outcome. More specifically, the invention relates to the application of the device in the therapy of visual and blood-related disorders. For example, there is a need for a device useful in the treatment of disorders including, but not limited to, glaucoma, coagulation of blood vessels in the skin, and retinal vein occlusion.

BACKGROUND OF INVENTION

Lasers are being used for variety of applications including stimulation, gene delivery and surgery of cells and tissues under direct visual, microscopic or endoscopic observation. However, layer-specific laser micromanipulation of tissues requires three-dimensional image guidance, which does not exist to date.

Optical coherence tomography (hereafter OCT) is an imaging modality which utilizes low coherence interferometry to acquire depth-resolved sample reflectivity profiles. OCT is an emerging technology for a wide range of biomedical applications, with its largest impact in the field of ophthalmology where its cross-sectional images of ocular tissue have become the gold standard for assessing morphology and abnormalities[1-4]. Due to its excellent axial resolution, OCT has been often jointly used with a variety of other optical techniques in a multimodal platform for enhanced characterization of biological tissues. Though OCT has been used to monitor the effect of a surgical laser beam on tissue, it is primarily used via free-space coupling with the OCT probe beam with separate scanning control. This limits the applicability of the method for in-vivo use and may be translatable to surface structures (e.g., cornea).

The efficient and targeted delivery of impermeable therapeutic molecules into retinal cells is of immense importance for therapy of various visual disorders. Delivery of opsin encoding genes to the retina has potential for vision restoration in patients with retinal degeneration and has advantages over electrical stimulation by providing higher (cell) resolution, cellular specificity without requiring intraocular surgery. Traditional methods for gene delivery require viral transfection or use of physical and chemical methods which suffer from one or more drawbacks such as invasiveness, low efficiency, and lack of spatially targeted delivery, and have deleterious effects such as unexpected inflammatory responses, immunological reactions. Further, for effective therapy of visual disorders involving geographic atrophies (GA) of the retina, it requires to localize the delivery of the targeted molecules to specific atrophied regions. There is an imminent need for development and optimization of a new and efficient non-viral method that can deliver therapeutic molecules to spatially targeted regions of the retina or other desired tissues in a minimally invasive manner.

In recent years, there has been a growing need for noninvasive neural stimulation and activity imaging for multitude of applications ranging from basic research to clinical diagnosis/therapy. Image guided stimulation of specific brain area and functional monitoring is desirable for an ideal neuro-modulationdevice. In vivo imaging of the cortical layers and the vascular network using conventional microscopy imaging is challenging. Optical Coherence Tomography (OCT) is a non-invasive imaging platform capable of depth resolved imaging of the cortical brain regions with high spatial resolution. Though neurovascular changes have been studied by quantification of blood flow using OCT, direct measurement of neural activities using OCT has not been achieved yet in in-vivo. Feedback-based precise neural stimulation is important in basic and applied neuroscience research with clinical implications, such as probing brain circuits, studying biological mechanisms of diseases, and treating neurological or psychological disorders.

SUMMARY OF THE INVENTION

To meet the challenges, the present invention provides a 3D image-guided laser microirradiation device which would facilitate the precision ablation at the targeted site and would enable the delivery of the therapeutic molecules to the biological tissue as well as can have applications in structural/functional imaging and feedback-controlled label-free IR stimulation platform that will provide non-contact activity/temperature monitoring without requiring dye or genetic sensitization.

According to an aspect of the present invention, there is provided a device comprising:
  a. a laser irradiation sub-assembly configured to generate a laser beam for irradiation of a sample comprising at least one of living tissue, neurons, retina cells, brain cells, heart cells, muscle cells, and skin cells;
  b. a visible light source combinable with the laser beam by a beam combiner and configured to at least one of: locate the laser beam;

stimulate the sample; and
fixate the sample;
c. an imaging light source sub-assembly which emits a light beam with a selected wavelength in a range from 400 nm to 1600 nm, wherein the selected wavelength is not perturbative to the functioning or structure of the sample;
d. wherein the light beam emitted from the imaging light source sub-assembly is combinable with the laser beam and able to be split by a beam splitter to generate a split combined beam having a first part and second part;
e. wherein the first part of the split combined beam is guided via an optical system comprising at least one mirror, at least one focusing element and at least one lens to irradiate the sample;
f. wherein the at least one mirror and at least one focusing element is actuatable to control the position and size of an irradiation spot on the sample;
g. wherein back-scattered light from the sample is able to pass through the optical system and the beam splitter to a detector;
h. wherein the second part of the split combined beam is able to traverse through an optical sub-assembly comprising a reference arm;
i. wherein optionally, back-reflected light from the reference arm is able to pass through the beam splitter to the detector to interfere with the back-scattered light from the sample;
j. wherein a signal from the detector is processed to obtain at least one of:
a depth-resolved image of the sample;
measurements of physical properties of the sample; and
measurements of physiological properties of the sample;
k. wherein a laser beam irradiation dose and pattern in a targeted region is controllable for performing at least one of ablation, stimulation, molecular delivery and alteration of the sample; and
l. wherein a dose and pattern of the light beam from the visible light source is controllable and able to be synchronized with the imaging light source for mapping functional properties of the sample.

The device may comprise an average laser beam power at a sample plane which is up to 1 Watt.

The wavelength of the laser beam may range from 300 nm to 2200 nm.

The laser beam may comprise pulses ranging from femtoseconds to seconds.

It may be that the visible light source is operable to emit light with a wavelength ranging from 400 to 700 nm and a power at a sample plane up to 10 mW.

The device may comprise an imaging light power at a sample plane which is below 10 mW.

The beam combiner and beam splitter may be based on any one of: a fiber-optic beam splitter, a wavelength division multiplexor, or a free-space optics, which is optimized for polarization and wavelength of the laser or light beam.

The back-scattered light from the sample may be elastically scattered light or inelastically scattered light, and measurable by a band pass or high pass optical filter.

The detector may be selected from at least one of a single photodetector, a linear array of photodetectors, a photomultiplier tube, a camera, and a spectrometer.

The physical properties may include reflectivity, changes in refractive index, temperature, topography and thickness of layer(s);

a. wherein the reflectivity may be measured from the intensity of image(s) of a sample layer(s) at different depth (s) acquired from the back-scattered light from the sample;
b. wherein the changes in refractive index may be estimated from the optical path difference measured by the interference of the imaging light beam backscattered from the sample with a reference beam;
c. wherein the temperature may be calculated from the changes in the optical path difference;
d. wherein the topography and thickness of different layers may be measured from the depth-resolved image(s) of the sample.

The monitoring of physiological properties may comprise analyzing the electrical response of the sample measured by electrode(s) with or without stimulation by the light from the visible light source, or by analyzing the properties comprising intensity, phase and fluorescence of back-scattered sample beam measured by the detector.

The laser beam irradiation may be capable of performing selective ablation by absorption of the targeted sample or dielectric breakdown of the sample in focused volume.

The laser beam irradiation may be capable of perforating the sample to allow delivery of impermeable molecules comprising at least one of drugs, proteins, and nucleic acids.

The laser beam irradiation may be capable of stimulation of the sample by electronic excitation of specific molecules of the sample or increasing temperature of the sample.

The visible light source may be configured to stimulate the sample by electronic excitation of specific molecules of the sample for probing the functioning of the sample or therapeutic use.

The laser beam may be integrated with a slit lamp or scanning laser Ophthalmoscope for fundoscopy of a subject's eye to identify region(s) of interest in a retina that requires Nano-enhanced Optical Delivery (NOD) by use of light-enhancing nanoparticles.

The laser beam may be integrated with optical coherence tomography for identifying retinal pathologies and providing feedback to the NOD laser beam delivery.

The device may comprise an NIR laser for NOD that is spatially sculpted by spatial light modulator or digital micromirror device to enhance throughput and match the shape(s) of the region(s) of interest in the tissue of a moving organ requiring targeted molecular delivery by NOD.

A wave front of an NIR laser beam for NOD may be corrected to account for distortions arising due to scattering properties of target tissue and imperfect optical media of the eye.

NOD may be improvised by use of adjunctive for stabilization of to-be-injected molecules, or enhancement of their binding or mobility, permeability of inner limiting membrane, or minimization of cellular damage.

The device as defined herein for use in the treatment of glaucoma, or for use in blood vessel removal from skin and eyes. This may involve treatment of coagulation of blood vessels and/or removing blood vessel from skin and eyes; including treatment of retinal vein occlusion.

In an embodiment, the present invention describes a device wherein 3D OCT image guiding modality is achieved in a spectral domain by use of low coherence broadband light source and spectrograph-camera detector, but can be achieved by swept-source combined with point detector.

In another embodiment, the present invention describes a device comprising an OCT integrated with microirradiation laser beams of different wavelengths in visible and infrared spectrum and operation modes (CW and pulsed) for targeted ablation and monitoring of the changes to microstructure due to ablation.

In yet another embodiment, the present invention describes a device comprising an OCT integrated with a microirradiation laser of varying wavelengths and operation modes for targeted stimulation.

In yet another embodiment, the present invention describes a device comprising an OCT integrated with a microirradiation laser of different wavelengths and operation modes for monitoring changes in cellular activities, stimulated by targeted microirradiation.

In another embodiment, the present invention describes a device for use in a method wherein the said device's phase-sensitive OCT modules would allow not only monitoring of the functional changes after targeted modulation, but will also record the localized temperature rise upon laser irradiation.

In yet another embodiment, the present invention describes a device comprising an OCT integrated with a microirradiation laser of varying wavelengths and operation modes for causing localized injury to mimic pathophysiology of disease or to achieve a therapeutic outcome such as decrease in intraocular pressure by trabeculoplasty or iridectomy.

In yet another embodiment, the present invention describes a device comprising an OCT integrated with a microirradiation laser of different wavelengths and operation modes for causing targeted gene/molecular delivery for altering the properties of tissue and/or for a therapeutic outcome.

In yet another embodiment, the present invention describes a device comprising an OCT guided microirradiation laser integrated with an electrophysiology system with different stimulation wavelengths and operation modes measuring physiological improvement due to OCT-guided laser ablation, surgery, gene delivery or microirradiation.

In yet another embodiment, the present invention describes an OCT-guided laser microirradiation device which can induce layer-specific damage to photoreceptors or neural retina or retinal pigment epithelium (RPE) without damaging the other layers.

In another embodiment, the present invention describes a device for use in a method, wherein said OCT guided integrated laser device can generate a model for dry-AMD. The irradiation laser is absorbed by the retina to generate high thermal gradient to damage the irradiated region, and the laser micro irradiation can be spatially targeted and guided to the region of interest (ROI) by OCT imaging guidance.

In another embodiment, the present invention describes a device for use in a method, wherein the said OCT guided microirradiation with laser of different wavelengths and operation modes can generate a model for retinitis pigmentosa or cone-rod dystrophy by selectively damaging rods or cone photoreceptors.

In another embodiment, the present invention describes a OCT guided laser device for micro-focal stimulation with different wavelengths to monitor activities of specific cell types such as rod or (S, M, L) cone functions in a retina.

Another aspect of this invention describes a device for use in a method wherein the said device's low-power near-infrared (NIR) laser beam (guided by OCT) is applied to permeabilize the cell membrane, which enables the delivery of therapeutic molecules into the cells.

In another embodiment, the present invention describes a device for use in a method wherein the said device enables highly precise delivery of therapeutic molecules including proteins, therapeutic genes, CRISPR/Cas9 gene editing agents, shRNA, microRNAs, and biomolecules to treat several diseases.

In a broader embodiment, this invention provides novel device integrating Optical coherence tomography (OCT) and VIS-NIR laser microirradiation for targeted ablation, stimulation, molecular delivery and therapy. Specifically, the invention relates to application of the device in therapies needing OCT guided targeted and precise surgeries, stimulations of various tissues, delivery of biological molecules including but not limited to DNA, RNA, SiRNA, CRISPR editing agents, and proteins leading to better visualization of a structure or process and/or for therapeutic outcome.

It is contemplated that any embodiment of a method, device or composition described herein can be implemented with respect to any other method, device or composition described herein.

Details associated with the embodiments described above and others are described below.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

FIG. 6A. B-scan OCT image of retina of a wild type mouse;

FIG. 6B. OCT-guided targeted laser-injury of Retinal Pigment Epithelium (RPE), displayed by decrease in contrast of RPE layer (marked by arrow) indicates damage to RPE layer. Photoreceptor layer (PRL) is still intact, but detached from the damaged RPE layer;

FIG. 6C. Enface OCT image of mice retina after OCT-guided targeted damage to RPE-layer. The injured region is marked by dashed white line ellipse;

FIG. 7A. Representative B-scan OCT image of the mouse retina after OCT-guided laser transfection (region marked by dashed arrows);

FIG. 7B. OCT en-face image showing OCT-guided ultrafast laser transfection area (marked by dashed rectangle);

FIG. 7C. Fluorescence image of transfected retina 1 week after OCT-guided in-vivo ultrafast laser transfection of large ABCA4-GFP plasmids (13 kb), showing reporter (GFP) fluorescence (in green), co-stained with nuclear stain (DAPI: Blue);

FIG. 7D. Zoomed-in fluorescence image of the OCT-guided ultrafast laser transfection targeted region (marked by rectangle in FIG. 8C;

FIG. 7E. Area of retina not targeted by OCT-ultrafast laser beam shows no characteristic fluorescence of reporter (GFP);

FIG. 8A. Retina thickness measured by OCT after OCT-guided femtosecond laser delivery of genes to retina, compared with thickness before laser delivery in retinal degenerated mice (control);

FIG. 8B. Reporter (mCherry) expression in targeted RGC layer, 2 weeks after OCT-guided femtosecond laser transfection;

FIG. 8C. Electroretinogram (ERG) response upon white light stimulation of retinal degenerated mice (control);

FIG. 8D. ERG response 1 week after OCT-guided femtosecond laser transfection of Multi-Characteristic opsin (MCO);

FIG. 8E. Visually evoked Potential (VEP) in retinal degenerated mice after OCT-guided femtosecond laser transfection of retina with MCO compared with that of control. $*p<0.05$;

FIG. 11A. In-vivo experimental set up for NOD in eye. To minimize non-specific binding, the gold nano-rods are PEGylated. The PEGylation also prevents the aggregation of the gold nano-rods in the vitreous. FIG. 11B shows pupil dilation imaged by laser scanning microscopy. FIG. 11C shows the zoomed image of eye during the laser exposure to near-infrared laser beam. FIG. 11D shows in-vivo expression of Opsin in retina cells in targeted region;

DETAILED DESCRIPTION OF THE INVENTION

Figure 1:
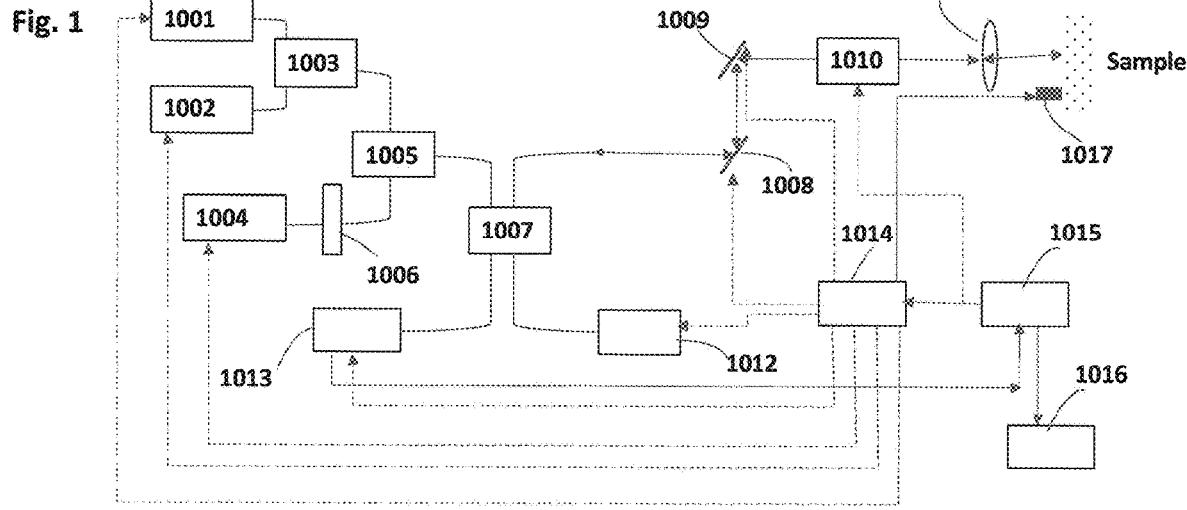
FIG. 1. 3D IMAGE GUIDED SCANNING IRRADIATION AND PHYSIOLOGY SYSTEM FOR TARGETED ABLATION, STIMULATION, MANIPULATION, MOLECULAR DELIVERY AND PHYSIOLOGICAL MONITORING. 1001: Laser; 1002: Visible Light Source; 1003: Beam Combiner-1; 1004: Imaging light source; 1005: Beam Combiner-2; 1006: Laser isolator; 1007: Beam Splitter; 1008: Mirror-1; 1009: Mirror-2; 1010: Dynamic Focusing Element; 1011: Focusing Lens(es); 1012: Reference arm; 1013: Detector; 1014: Microcontroller; 1015: Computer; 1016: Display; 1017: Electrode(s)

Lasers are being used for variety of applications including stimulation, gene delivery and surgery of cells and tissues under direct visual, microscopic or endoscopic observation. However, layer-specific laser micromanipulation of tissues requires three-dimensional image guidance, which does not exist to date.

Though OCT has been used to monitor effect of surgical laser beam on tissue, it is primarily via free-space coupling with the OCT probe beam with separate scanning control. This limits the applicability of the method for in-vivo use and may be translatable to surface structures (e.g., cornea) only. OCT guided spatially targeted infrared laser irradiation platform presented here provides localized injury leading to layer-specific retinal degeneration and real-time monitoring of such laser-induced injury related structural changes.

Full-field flash Electroretinogram (ERG) has enabled measurement of overall retinal function. However, non-severe retinal defects at early stages of the disease may not be detected by full-field (Ganzfield) ERG measurements. The existing focal ERG is based on large spot size stimulation and therefore, cannot provide functional information at resolution necessary to evaluate therapeutic efficacy at cellular level, e.g., along edges of a transplant. Similarly, the multifocal ERG (mfERG) method that provides a topographical measure of retinal activity, cannot isolate function at single cell level. Further, the focal ERG and mfERG illumination use white light and therefore, cannot distinguish different cone functions. There is a clear need for development of ERG based on multi-color micro-focused laser stimulation to discern cellular changes at high resolution, thus allowing critical evaluation of disease progression and therapeutic intervention in retina. By OCT guided focal ERG measurements at multiple stimulation wavelengths using the integrated device, pathophysiological progression of laser-injured atrophic regions could be evaluated as presented in this invention. OCT guided laser based targeted irradiation enabled development of animal models of human diseases but also allowed non-viral gene therapy while characterizing the disease progression and recovery.

The efficient and targeted delivery of impermeable therapeutic molecules into retinal cells is of immense importance for therapy of various visual disorders. Traditional methods for gene delivery require viral transfection or use of physical and chemical methods which suffer from one or more drawbacks such as invasiveness, low efficiency, and lack of spatially targeted delivery, and have deleterious effects such as unexpected inflammatory responses, immunological reactions. Further, for effective therapy of visual disorders involving geographic atrophies (GA) of the retina, it requires to localize the delivery of the targeted molecules to specific atrophied-regions identified by Optical Coherence Tomography (OCT). Therefore, the 3d image guided laser microirradiation inventive device described here provides reliable detection of anatomical alterations of the retina and delivery of therapeutic molecules into targeted GA areas.

Precise neural stimulation based on feedback from imaging/activity is important in basic and applied neuroscience research with clinical implications, such as probing brain circuits, studying biological mechanisms of diseases, and treating neurological or psychological disorders. Therefore, as a better alternative to electrical or other approaches, there is growing interest in non-contact neural modulation using infrared light that does not require genetic sensitization. Further, there is a need to simultaneously detect physiological changes such as temperature and electrical activities while conducting the stimulation in a clinical setting.

To meet the challenges, the present invention provides a novel image-guided laser irradiation device which would facilitate the precision ablation at the targeted site and would enable the delivery of the therapeutic molecules to the biological tissue as well as can have applications in structural/functional imaging and feedback-controlled label-free IR stimulation platform that will provide non-contact activity/temperature monitoring without requiring dye or genetic sensitization.

In an embodiment, the present invention describes a device wherein 3D OCT image guiding modality is achieved in spectral domain by use of low coherence broadband light source and spectrograph-camera detector but can be achieved by swept-source combined with point detector.

In another embodiment, the present invention describes a device comprising an OCT integrated with microirradiation laser beams of different wavelengths in visible and infrared spectrum and operation modes (CW and pulsed) for targeted ablation and monitoring of the changes to microstructure due to ablation.

In yet another embodiment, the present invention describes a device comprising an OCT integrated with microirradiation laser of varying wavelengths and operation modes for targeted stimulation.

In yet another embodiment, the present invention describes a device comprising an OCT integrated with microirradiation laser of different wavelengths and operation modes for monitoring changes in cellular activities, stimulated by targeted m icroirradiation.

In another embodiment, the present invention describes a device for use in a method wherein the said device's phase-sensitive OCT modules would allow not only to monitor the functional changes after targeted modulation, but will also record the localized temperature rise upon laser irradiation.

In yet another embodiment, the present invention describes a device comprising an OCT integrated with microirradiation laser of varying wavelengths and operation modes for causing localized injury to mimic pathophysiology of disease or to achieve therapeutic outcome such as decrease in intraocular pressure by trabeculoplasty or iridectomy.

In yet another embodiment, the present invention describes a device comprising an OCT integrated with microirradiation laser of different wavelengths and operation modes for causing targeted gene/molecular delivery for altering the properties of tissue and/or for therapeutic outcome.

In yet another embodiment, the present invention describes a device comprising an OCT guided microirradiation laser integrated with electrophysiology system with different stimulation wavelengths and operation modes measuring physiological improvement due to OCT-guided laser ablation, surgery, gene delivery or m icroirradiation.

In yet another embodiment, the present invention describes a OCT-guided laser microirradiation device which can induce layer-specific damage to photoreceptors or neural retina or retinal pigment epithelium (RPE) without damaging the other layers.

In another embodiment, the present invention describes a device for use in method, wherein the said OCT guided integrated laser device can generate a model for dry-AMD. The irradiation laser is absorbed by the retina to generate high thermal gradient to damage the irradiated region, and the laser micro irradiation can be spatially targeted and guided to the region of interest (ROI) by OCT imaging guidance.

In another embodiment, the present invention describes a device for use in method, wherein the said OCT guided microirradiation with laser of different wavelengths and operation modes can generate a model for retinitis pigmentosa or cone-rod dystrophy by selectively damaging rods or cone photoreceptors.

In another embodiment, the present invention describes a OCT guided laser device for micro-focal stimulation with different wavelengths to monitor activities of specific cell types such as rod or (S, M, L) cone functions in retina.

Another aspect of this invention describes a device for use in a method wherein the said device's low-power near-infrared (NIR) laser beam (guided by OCT) is applied to permeabilize the cell membrane, which enables the delivery of therapeutic molecules into the cells.

In another embodiment, the present invention describes a device for use in a method wherein the said device enables highly precise delivery of therapeutic molecules including proteins, therapeutic genes, CRISPR/Cas9 gene editing agents, shRNA, microRNAs, and biomolecules to treat several diseases.

In a broader embodiment, this invention provides novel device integrating Optical coherence tomography (OCT) and VIS-NIR laser microirradiation for targeted ablation, stimulation, molecular delivery and therapy. Specifically, the invention relates to application of the device in therapies needing OCT guided targeted and precise surgeries, stimulations of various tissues, delivery of biological molecules including but not limited to DNA, RNA, SiRNA, CRISPR editing agents, and proteins leading to better visualization of a structure or process and/or for therapeutic outcome.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Throughout this application, the term "about" is used to indicate that a value includes the standard deviation of error for the device or method being employed to determine the value.

Further, a molecule or method that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps.

Any embodiment of any of the apparatuses, devices, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

To the extent that any specific disclosure in the aforementioned references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed or alleged herein.

Below, the presently disclosed invention will be further described by way of examples, which are provided for illustrative purposes only and accordingly are not to be construed as limiting the scope of the invention.

EXAMPLES

We have developed a three-dimensional imaging integrated with laser microirradiation device for multitude of physical, biological and biomedical applications. With real-time imaging capability, we perform structural as well as functional assessment and targeted alteration, stimulation, manipulation of living tissues or non-living material.

Example 1

FIG. 1 shows the schematic of Optical Coherence Tomography (OCT) based 3D image guided scanning irradiation and physiology system for targeted ablation, stimulation, manipulation, molecular delivery and physiological monitoring. The NIR laser beam (1001) was combined with the Visible Light from a laser/LED Source (1002) using a Beam Combiner-1 (1003). The NIR laser beam is used for targeted alteration, stimulation, manipulation of living tissues or non-living material. The visible light (from a blue-green-red laser) was used for stimulation. A low coherence light from imaging source (1004) with center wavelength 860 nm and bandwidth: ~70 nm was combined with the NIR laser (980 nm) beam and Visible light beam using a second Beam Combiner-2 (1005). A Laser isolator (1006) was used to block any back-reflected NIR or Visible laser beam going into the imaging light source. A 50/50 Beam Splitter (1007) was used to split the NIR and visible laser beam to two arms. The beam in the sample arm is guided and scanned using Mirror-1 (1008) and XY MEMS Mirror-2 (1009). The Dynamic Focusing Element (1010, a Liquid lens) in combination with an assembly of Focusing Lenses (1011) was used to focus the NIR and visible laser beams on to the sample. The second beam from the Beam Splitter (1007) serves as Reference arm with adjustable path length (1012) consisting of collimating lens and mirror to back-reflect the reference beam to the Beam Splitter (1007). The back-scattered light from the sample is routed through the assembly of Focusing Lenses (1011), Dynamic Focusing Element (1010), XY MEMS Mirror-2 (1009) and Mirror-1 (1008) to the Beam Splitter (1007), wherein the back-scattered light from the sample was split and collected by a Detector (1013). The back-reflected reference beam after splitting at the Beam Splitter (1007) was also collected by the Detector (1013), comprising of a spectrograph-camera. The interference signal between the back-reflected signal from the reference mirror and the back-scattered light signal from the sample is detected with the spectrograph-CCD detector as a function of wavelength. The detected signal (as a function of wavelength) is then Fourier transformed to obtain tomographic information, i.e. intensity profile as a function of depth. In order to achieve scanning irradiation for targeted ablation, stimulation, manipulation, molecular delivery and physiological monitoring, user-friendly GUI software was used to control the OCT-sensor, obtain measurements, and view results. 3D rendering was carried in a software platform to simplify operation and allow real time adjustment of OCT imaging location and acquisition. The software control panel was used for changing the power and exposure time (scan rate) of the NIR, visible laser beams and OCT imaging beam. A Microcontroller (1014) and Computer (1015) with Display (1016) was used to control and automate the NIR laser (1001), Visible laser (1002), low-coherence imaging light source (1004), XY MEMS Mirror-2 (1009), the Reference arm with adjustable path length (1012), and the Detector (1013). Electrodes (1017) were used on the sample (eye, brain, skin) to measure the electrophysiological activities of tissue while performing 3D image-guided laser stimulation.

The integrated device enabled easy-to-use OCT guided laser microirradiation and Electroretinography (ERG)/Visually evoked potential (VEP, when electrodes are placed in brain/over visual cortex) measurement workflow in one multi-modal platform setting. OCT provided good depth penetration along with excellent depth resolution, and OCT integrated with ERG allowed depth resolved and spatially targeted focal stimulation. ERG measurement provided the electrical responses of various cell types in the retina, including the photoreceptors, inner retinal cells and the retinal ganglion cells. Various modes of laser stimulation were carried out for different ERG measurements, such as global stimulation, focal stimulation, flickering stimulation, and patterned stimulation in order to access selective functional information of retina. For measuring label-free opto-elctrophysiology, the phase of the intereference signal was masured. Synchronized micro-focal Phase OCT measurements during stimulation allowed sub-wavelength nanoscale displacement measurements. Easy-exchangeable imaging lens allowed imaging and irradiation of wide range of species: small (mouse, rat) to large animals (rabbit, pigs/NHP) and human. On the other hand, upon focused illumination of multi-color laser beams, evoked responses in different retinal layers in multiple areas of retina are measured to quickly determine which area of the retina produce abnormal functional response as well as fine navigating the focal stimulation to specific point.

Example 2

Figure 2A:
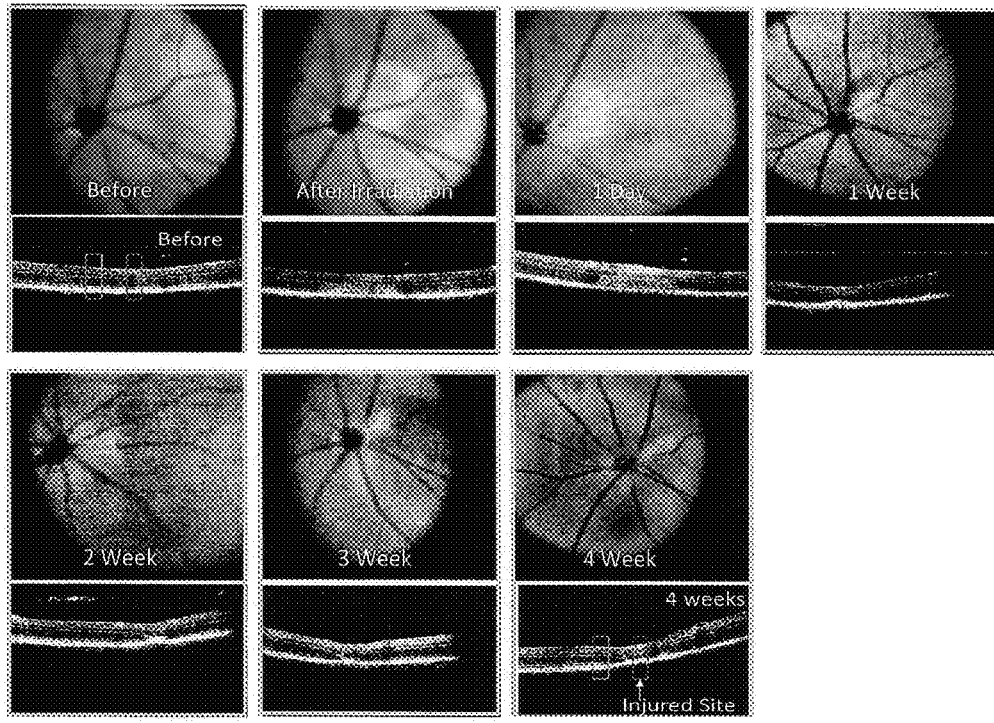
FIG. 2A. OCT-guided targeted laser-injury, loss of photoreceptor layer leading to thinning of retina. Initial swelling of PR layer is visible in OCT enface image as bright. Damaged Photoreceptor layer and associated progressive thinning of retina. No change in contrast of RPE layer.
Figure 2B:
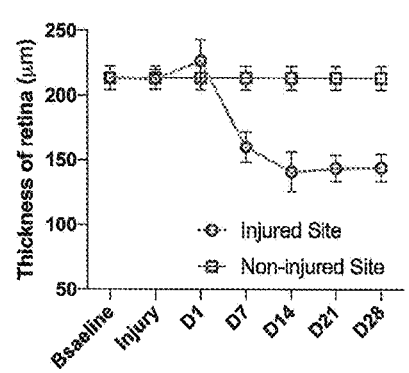
FIG. 2B. Quantitative comparison of progressive thinning of retina of laser-injured site and non-injured site.

The OCT guided laser microirradiation system was used to develop animal model of retinal degeneration. The advancement of new therapeutic interventions is dependent on availability of suitable animal models of retinal degeneration, especially geographic atrophic (GA) areas as in dry-AMD. The suitability includes the degree to which the animal model emulates critical aspects of GA in human, including damage to the cones (major photoreceptors in macula) in retina. For localized photoreceptor degeneration similar to dry age-related macular degeneration (dry-AMD), OCT guided laser microirradiation of a selected area near the optic nerve was carried out with beam focused on the photoreceptor layer. Wild type mice (C57BL/6J) were obtained from Jackson laboratory. Mice were maintained on a 12:12 light cycle (lights on at 07:00). For in-vivo laser injury experiments, mice were anesthetized with 90 mg/kg ketamine, 10 mg/kg xylazine and acepromazine (0.5 mg/kg). After identifying the target area of retina using OCT imaging, the MEMS-scanner is programmed to shape the laser scanning area for injury. The NIR laser beam power at the sample plane was varied from 1 to 100 mW and the injury dimensions ranged from small GA (~0.05 mm) to 2 mm, covering the whole retina. Longitudinal OCT images were taken prior to laser microirradiation and for 4 weeks after the laser injury. FIG. 2A shows OCT-guided targeted laser-injury, loss of photoreceptor layer leading to thinning of retina. Initial swelling of Photoreceptor layer (PRL) is visible in OCT enface image as bright. The photoreceptor layer in the OCT images shows higher contrast right after irradiation and thinning at the targeted region. No change in contrast of Retinal Pigment Epithelium (RPE) layer was observed. FIG. 2B shows quantitative comparison of progressive thinning of retina of laser-injured site and non-injured site. Longitudinal OCT measurements showed progressive degeneration of photoreceptors within lesions, but an unaffected inner nuclear or retinal ganglion cell layer. Since the OCT beam shares the identical optical path with the optical microirradiation beam and provides capability to locate region of interest for injury, and to monitor changes in real time. We observed underlying fibrosis and abnormal apical-basal RPE surfaces. While for highly localized injury of PRL, the RPE became hypo-reflective, severe laser-induced atrophy led to hyper-reflective RPE and Bruch's membrane thickening.

Example 3

Figure 3A:
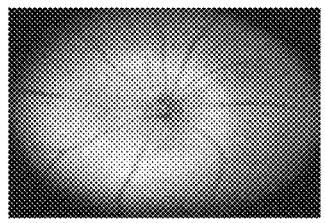
FIG. 3A. Enface OCT image of a mice retina.
Figure 3C:
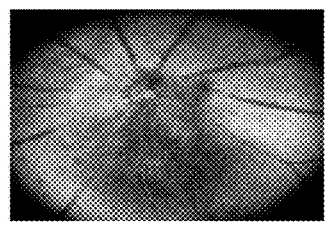
FIG. 3C. Enface OCT image of a mice retina after OCT-guided targeted photoreceptor damage.
Figure 3B:
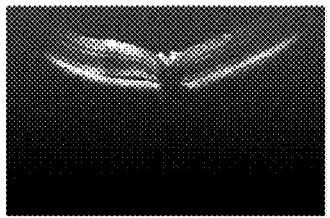
FIG. 3B. B-scan OCT image of mice retina.
Figure 3D:
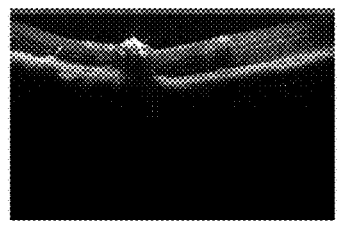
FIG. 3D. B-scan OCT image after OCT-guided targeted photoreceptor damage by laser.
Figure 3E:
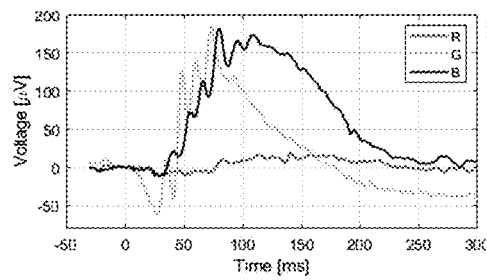
FIG. 3E. Scotopic micro-focal Electroretinography (fERG) response from the uninjured retina region showing typical ERG response at three different wavelengths.
Figure 3F:
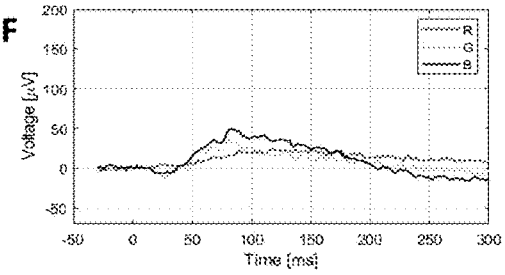
FIG. 3F. Functional deficits in the Dry-AMD mouse model created by OCT-guided Laser injury, measured by focal ERG. Scotopic fERG response from the GA (laser-damaged) region showing diminished ERG response.

FIG. 3A shows Enface OCT image of a mice retina and FIG. 3B shows B-scan OCT image of mice retina. The OCT guided laser microirradiation integrated electrophysiology system was used to measure functional deficits in the Dry-AMD mouse model created by OCT-guided Laser injury, was measured by integrated focal ERG. FIG. 3C shows Enface OCT image of a mice retina after OCT-guided targeted photoreceptor damage and FIG. 3D shows B-scan OCT image after OCT-guided targeted photoreceptor damage by laser. Evaluation of the pathophysiological progression of GA in the injured retina was carried out using OCT and micro-focal electroretinography (mfERG) with selected stimulation wavelengths for S, M and L cone-opsins. A subcutaneous needle inserted in the back of the head served as the reference electrode. Visual illumination was presented separately for 1 ms, with ≥1 s between stimuli. Further, to determine relative damage to specific cones, spectral fERG measurements were carried out. Visual illumination with center wavelengths in blue (450 nm), green (530 nm) and red (630 nm) over a range of intensities was presented separately to measure activities in control regions as well as OCT-guided laser-injured regions. Scotopic micro-focal Electroretinography (fERG) response from the uninjured retina region showing typical ERG response at three different wavelengths is shown in FIG. 3E. FIG. 3F shows Functional deficits in the Dry-AMD mouse model created by OCT-guided Laser injury, measured by focal ERG. Scotopic fERG response from the GA (laser-damaged) region showing diminished ERG response. Evaluation of the pathophysiological progression of laser-injured atrophic regions using OCT and focal ERG measurements at multiple stimulation wavelengths showed significant reduction in functioning of GA as observed in human conditions.

There often is a need to target specific or multiple retinal cell types to emulate the disease model. For example, in contrast to inherited retinal degenerative diseases and dry-AMD where photoreceptor and RPE damage occurs, Glaucoma is associated with damage to RGCs. For mimicking pathological progression of GA, or development of new atrophies, OCT guided spatiotemporal control of laser beam irradiation pattern and schedule provides unique opportunity. Further, while Retinitis Pigmentosa is associated with loss of rods preceding loss of cones, in case of cone-rod dystrophy loss of cones leads to loss of rods. By varying the wavelength of the OCT-guided laser-selective laser microirradiation beam allowed wavelength-selective injury to rods versus cones and even selective injury of specific (S, M, L) cones. The micro-focused laser injury approach based on continuous wave NIR laser beam is found to be minimally invasive with no detectable collateral damage to retina or other ocular elements as measured by OCT.

Example 4

Figure 4A:
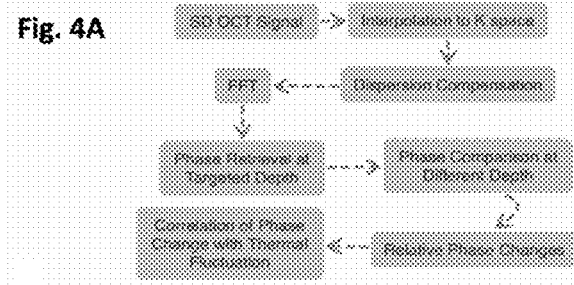
FIG. 4A. Flow diagram for OCT phase-based computation of thermal profile generated by OCT-guided infrared laser irradiation.
Figure 4B:
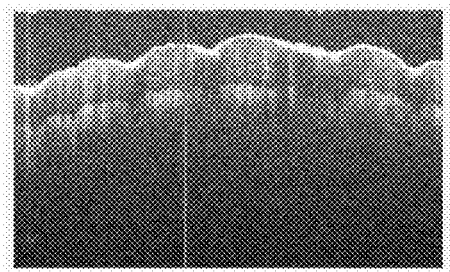
FIG. 4B. OCT B-scan image of tissue. Two horizontal red lines indicate the layers used to monitor changes in optical thickness.
Figure 4C:
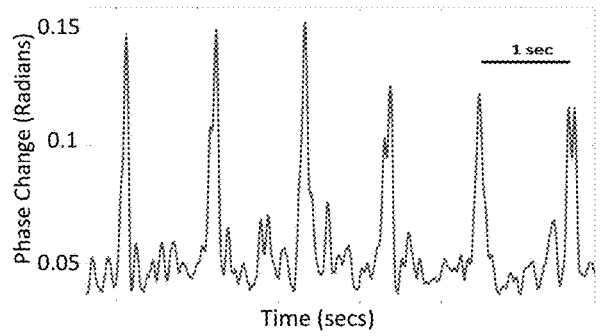
FIG. 4C. Optical phase signal change due to temperature rise in a brain tissue upon stimulation by infrared laser beam (40 ms pulses, 1 Hz)
Figure 4D:
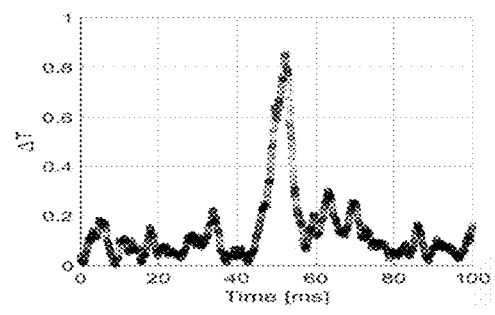
FIG. 4D. Estimated change in temperature of tissue (stimulated by infrared laser beam pulse) as a function of time.

In the OCT-guided laser microirradiation device described here, the contrast in temperature rise in laser-irradiated cells at micro-focused spots is significant enough to allow site and layer-specific injury (surgery) at high power and stimulation at lower power levels. OCT guided NIR laser-induced temperature rise also caused stimulation of neural tissues. The integrated OCT guided laser microirradiation device was used to measure subtle rise in temperature (by IR laser) in tissue using phase-sensitive OCT. Temperature rise is known to cause changes the refractive index of medium. In order to measure the sub-wavelength optical path length change induced by thermal stimulation, the phase angle of the depth-resolved complex interference signal (instead of magnitude) was computed. By taking the difference in phase derived above and below the sample-layer of interest, the relative change in phase signal was monitored. This information is used to extract thermal profile at the stimulated location in real time. FIG. 4A shows the Flow diagram for OCT phase-based computation of thermal profile generated by OCT-guided infrared laser irradiation. OCT B-scan image of tissue is shown in FIG. 4B shows the two horizontal red lines indicate the layers used to monitor changes in optical thickness. In FIG. 4C, we show the Optical phase signal change due to temperature rise in a brain tissue upon stimulation by infrared laser beam (40 ms pulses, 1 Hz). FIG. 4D shows the estimated change in temperature of tissue (stimulated by infrared laser beam pulse) as a function of time. The change in phase signal indicates small-scale changes in optical path length caused by change in index of refraction change within the measured volume. Thus, phase OCT integrated laser stimulation device was demonstrated to be capable of monitoring functional activity from the stimulated region. Two major feedbacks in the software to improve the measurement efficiency was (i) specific localization of stimulation from OCT imaging; and (ii) near real-time monitoring of temperature rise. We were able to acquire 3D volumetric OCT scan and navigate within the acquired volume to target the region of interest, while the cross-sectional OCT scan displayed. After stimulation spot is selected, the software prompts which two depths should be selected for phase difference measurement. Once the two depths of interest are determined, stationary OCT signal (M-scan) starts generating computed phase change and display in separate window with default B-scan frame rate. Finally, when the stimulation option is initiated with set pulse width and repetition rate, the interactive software provide insight about the stimulation status such as: (i) potential damage from bulk heating effect; and (ii) power adjust suggestions based on overall phase change calculation. The user-friendly GUI software provides a platform for user interaction, allowing the user to control the OCT image acquisition in multiple scanning mode: A-scan functional probing, B&C-scan for structural imaging for identifying stimulation location. The software allows navigation through the region of interest within OCT scan by adjustable scanning range and depth of focus. Within the same OCT software platform, the users have access to a control panel for customizing the stimulation laser such as power, pulse duration, frequency of stimulation and specific ROI selection within the OCT scan. When the stimulation-option is initiated, it prompts the user with a list of parameters and will guide the user through the delivery process. Thus, the integrated device and software provides 3D OCT image guided micro-focused laser stimulation control and temperature measurement. The software also provides easy analysis of raw M-scan data for probing functional (neural activities) changes by measuring phase OCT signal either offline or online.

Example 5

Figure 5A:
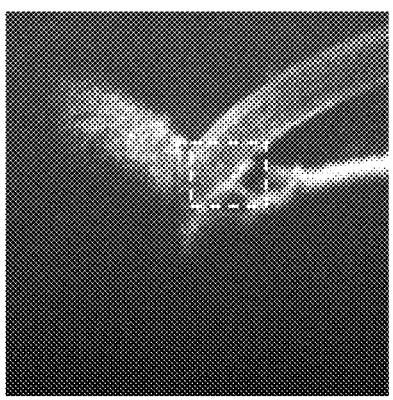
FIG. 5A. B-scan OCT image of trabecular meshwork (TM) of a mouse.
Figure 5C:
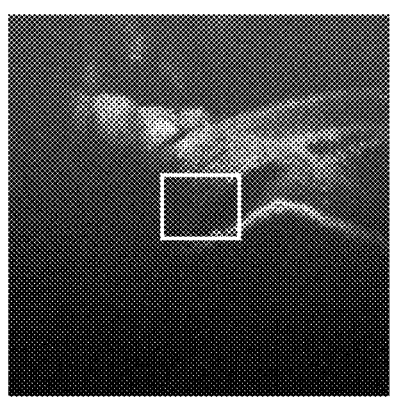
FIG. 5C. B-scan image of the TM after OCT-guided targeted laser surgery.
Figure 5B:
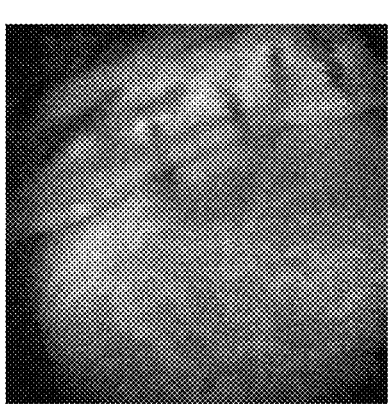
FIG. 5B. Enface OCT image showing cornea of a mouse.
Figure 5D:
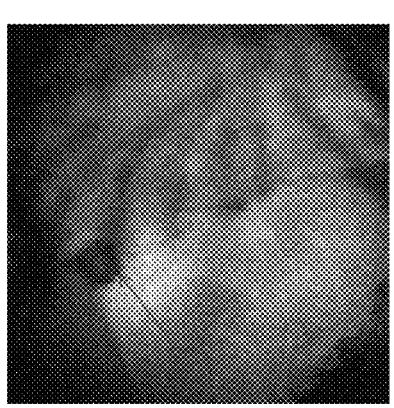
FIG. 5D. Enface OCT image showing Iridectomy near iridocorneal angle (at arrow marked site) using OCT-guided targeted laser surgery.

The OCT-guided laser microirradiation device was used for trabeculoplasty, which reduces intraocular pressure in glaucomatous eyes. FIG. 5A shows the B-scan OCT image of trabecular meshwork (TM, marked inside the dashed rectangle) of a mouse. FIG. 5B shows the Enface OCT image showing cornea of the mouse. The location of the scan can then be controlled by the user within the field of view of the enface OCT image. After identifying the target area of the TM, the MEMS-scanner is programmed to shape the laser scanning area for OCT-guided trabeculoplasty. The target area (0.1 mm×0.1 mm) is exposed to the focused (15 mm) laser beam. FIG. 5C shows the B-scan image of the TM after OCT-guided targeted laser irradiation (980 nm, 100 mW, 5 sec). The reduced contrast of the TM is visible after the OCT-guided laser trabeculoplasty. Besides selection of the desired trabeculoplasty area, power, pulse width and frequency for laser was varied to achieve optimal outcome, i.e., improvement of the outflow of fluid from the anterior chamber leading to lower intraocular pressure. In FIG. 5D, we show Enface OCT image showing Iridectomy near iridocorneal angle (at arrow marked site) using OCT-guided targeted laser surgery device. The OCT-guided laser microirradiation based trabeculoplasty will provide better control of open angle Glaucoma, Example 6

Figure 5E:
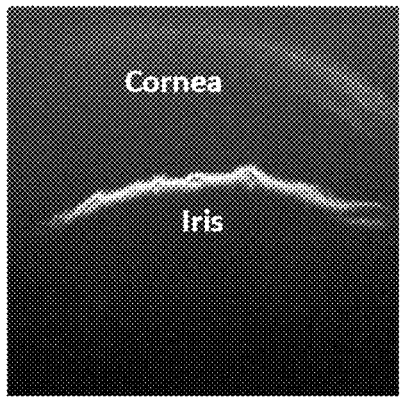
FIG. 5E. B-scan OCT image of Cornea and Iris of a mouse.
Figure 5F:
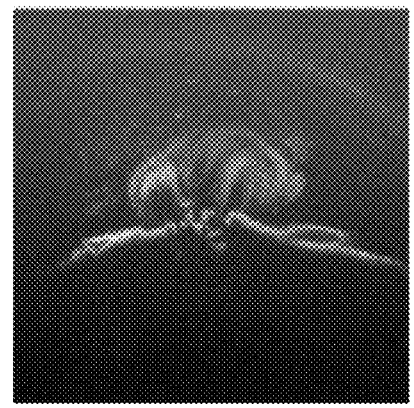
FIG. 5F. B-scan OCT image showing Iridectomy at arrow marked site using OCT-guided targeted laser surgery.
Figure 5G:
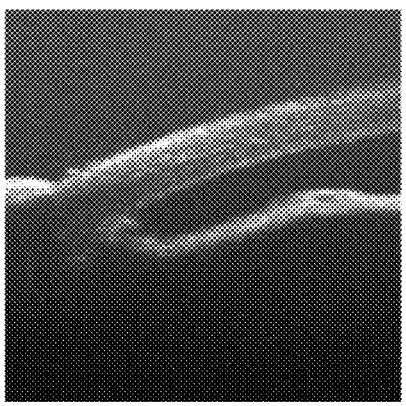
FIG. 5G. B-scan OCT image showing cornea and iris near the iridocorneal angle of a mouse.
Figure 5H:
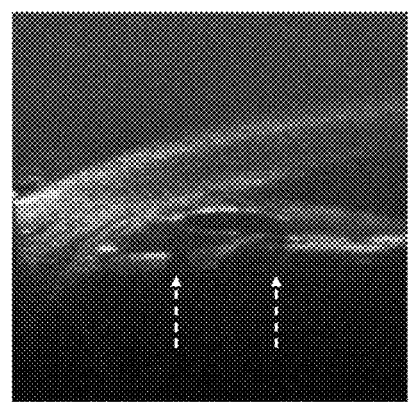
FIG. 5H. B-scan OCT image showing Iridectomy near iridocorneal angle (marked by 2 dashed arrows) using OCT-guided targeted laser surgery.

For closed angle glaucoma, the OCT-guided laser microirradiation device was used for iridoctomy, which reduces intraocular pressure in glaucomatous eyes. FIG. 5E shows the B-scan OCT image of Cornea and Iris of a mouse. After identifying the target area (0.1 mm×0.1 mm) of the iris, the MEMS-scanner is programmed (via GUI software) to shape the laser ablation area for OCT-guided iridoctomy. B-scan OCT image showing Iridectomy at arrow marked site using OCT-guided targeted focused (15 mm) NIR laser (980 nm, 100 mW, 5 sec) based surgery (FIG. 5F). The location of the hole in the iris was controlled within the field of view of the enface OCT image. FIG. 5G shows B-scan OCT image showing cornea and iris near the iridocorneal angle of a mouse. In FIG. 5H, we show B-scan OCT image of hole in the iris near the outer edge of the iris, (marked by 2 dashed arrows) using OCT-guided targeted laser surgery. The creation of precise hole using OCT-guided laser microsurgery leads to an opening of the angle in the majority of angle-closure glaucoma cases. After the angle is widened from OCT-guided laser iridectomy, the trabecular meshwork is exposed, and fluid outflow is enhanced.

Example 7

To increase the precision of OCT guided laser surgery, a Femtosecond NIR laser (1001, in FIG. 1) beam was used. FIG. 6A top and bottom panels respectively show B-scan OCT images of retina of a wild type mouse near and away from optic nerve. FIG. 6B top and bottom panels respectively show OCT-guided targeted laser (pulse width: 200 fs, Wavelength: 1060 nm, Frequency: 80 MHz, Average power: 60 mW) injury of Retinal Pigment Epithelium (RPE) of a wild type mouse near and away from optic nerve. The RPE damage was observed via a decrease in contrast of RPE layer (in arrow marked spot) displayed in real-time. Photoreceptor layer (PRL) was found to be still intact but detached from the damaged RPE layer. FIG. 6C shows the Enface OCT image of mice retina after OCT-guided femtosecond laser based targeted damage in the RPE-layer. The injured region is marked by dashed white line ellipse.

Example 8

Most of the non-viral approaches lack spatial and/or cellular specificity and limited by low transfection efficacy and cytotoxicity. In this regard, we have developed an efficient, safe, targeted, light-based OCT guided non-viral gene delivery device platform. Using the OCT-guided ultrafast laser based microirradiation device, we demonstrate non-viral delivery of large (ABCA4-GFP) genes to retina in-vivo. The wild type mouse was anesthetized using the mixture of 90 mg/kg ketamine, 10 mg/kg xylazine and 0.5 mg/kg acepromazine. Local anesthesia (proparacaine) was topically applied to the eye prior to intravitreal injection. The CAG-ABCA4-eGFP plasmid solution (1 µl) was injected by a sterilized 29-gauge needle of a Hamilton micro-syringe inserted through the sclera into the vitreous cavity (intravitreal injection). Ciprofloxacin (0.3%) eye drops were applied to the ocular surface following the intravitreal injection. The cornea was kept moist with a balanced salt solution during the entire surgical procedure. After the intravitreal injection of ABCA4 plasmids, Tropicamide (1%) was used to dilate the pupils of the mouse before optoporation. Within one-hour, optical gene delivery into the retina was carried out using the OCT guided ultrafast NIR laser microbeam. OCT images were acquired before and after OCT-guided ultrafast laser transfection to assess any apparent laser related damages. FIG. 7A shows a representative B-scan OCT image of the mouse retina after OCT-guided laser transfection (region marked by dashed arrows) using femtosecond laser microbeam (pulse width: 200 fs, Wavelength: 1060 nm, Frequency: 80 MHz, Average power: 20 mW). The OCT en-face image showing OCT-guided ultrafast laser transfection area (marked by dashed rectangle) is shown in FIG. 7B. FIG. 7C is a representative fluorescence image of transfected retina 1 week after OCT-guided in-vivo ultrafast laser transfection of large ABCA4-GFP plasmids (13 kb), showing reporter (GFP) fluorescence (in green), co-stained with nuclear stain (DAPI: Blue). In FIG. 7D, we show zoomed-in fluorescence image of the OCT-guided ultrafast laser transfection targeted region (marked by rectangle in FIG. 7C). Area of retina not targeted by OCT-ultrafast laser beam shows no characteristic fluorescence of GFP-reporter (FIG. 7E). Monitoring of intraocular pressure at baseline and after ultrafast laser transfection showed no adverse changes. Further, absence of any immune response in retina subsequent to OCT guided ultrafast laser transfection provides unique opportunity for targeted and repeated dosing of tissues in-vivo.

Example 9

In this example, we show that in-vivo OCT-guided femtosecond laser transfection of Multi-Characteristics opsin (MCO) genes in targeted area of retina led to functional expression and electrical activity. The femtosecond average laser power at the sample plane 20 mW (pulse width: 200 fs, Wavelength: 1060 nm, Frequency: 80 MHz). Monitoring of retina thickness by OCT at baseline and after OCT guided ultrafast laser transfection showed no significant changes. FIG. 8A shows the retina thickness measured by OCT after OCT-guided femtosecond laser delivery of genes to retina, compared with thickness before laser delivery in retinal degenerated mice (control). In FIG. 8B, we show reporter (mCherry) expression in targeted RGC layer, 2 weeks after OCT-guided femtosecond laser transfection. Monitoring of electroretinogram at baseline and after ultrafast laser transfection showed improved signal in retinal degenerated mice and no adverse changes in wild type mice. FIG. 8C shows electroretinogram (ERG) response upon white light stimulation of retinal degenerated mice (control). In FIG. 8D, we show ERG response 1 week after OCT-guided femtosecond laser transfection of Multi-Characteristic opsin (MCO). FIG. 8E. shows Visually evoked Potential (VEP) in retinal degenerated mice after OCT-guided femtosecond laser transfection of retina with MCO compared with that of the control. Statistically significant improvement in VEP signal was found in mice with retina transfected with MCO by OCT guided ultrafast laser gene delivery device.

Example 9B

Figure 9A:
FIG. 9A. B-scan OCT image of wild type mouse retina at baseline.
Figure 9B:
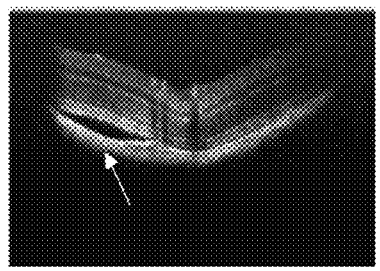
FIG. 9B. B-scan image of the retina immediately after OCT-guided laser irradiation, leading to detachment of retina (marked by arrow)
Figure 9C:
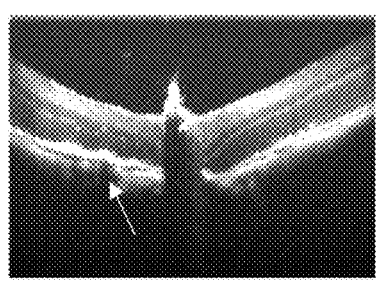
FIG. 9C. B-scan image of the retina 10 days after OCT-guided localized laser injury. The arrow points to thinning of retina (due to loss of photoreceptors) and hyperreflective RPE-Buch's membrane.
Figure 9D:
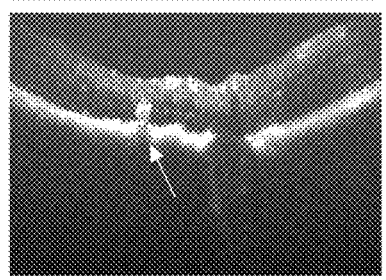
FIG. 9D. B-scan image of the retina 2 weeks after OCT-guided localized laser injury. Thinning of retina, hyperreflective RPE-Buch's membrane and fibrosis is visible. The arrow points to the injured region, where nano-enhanced optical delivery (NOD) of Multi-Characteristic Opsin (MCO) plasm ids was carried out.
Figure 9E:
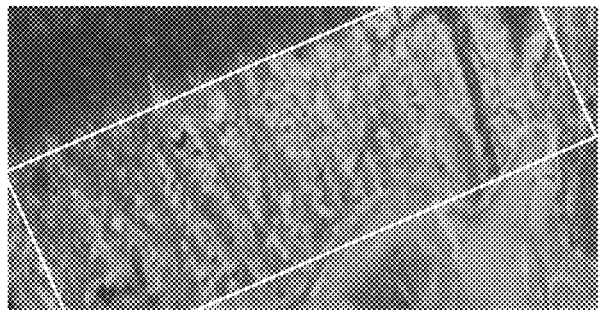
FIG. 9E. OCT-guided targeted NOD of MCO-mCherry led to expression of reporter (mCherry, immunostained with green fluorescent secondary antibody) in the targeted region (marked by white rectangle)
Figure 9F:
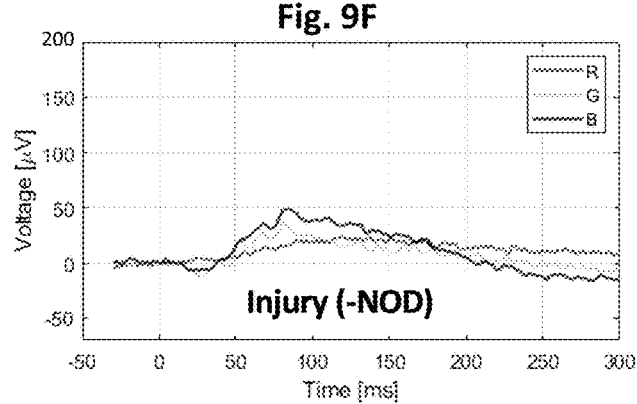
FIG. 9F. Scotopic focal ERG response obtained using blue (B), green (G) and red (R) light stimulation from a targeted photoreceptor damaged region showing diminished A and B-waves.
Figure 9G:
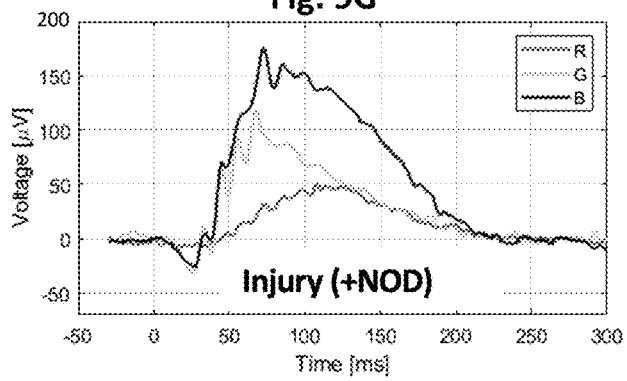
FIG. 9G. OCT-guided targeted NOD of polychromatic opsin (MCO) led to improved blue/green/red stimulated focal ERG in the area injured by OCT-guided laser injury.

In order to enhance the performance of the OCT guided laser gene delivery device, and to be able to utilize continuous wave laser beam instead of femtosecond laser beam, nanoparticles were added to the to-be-delivered genes and injected to the tissue of interest. Addition of functionalized nanoparticles enhanced the local intensity by surface plasmon resonance. For OCT guided laser gene delivery, the laser is coupled with OCT system such that OCT provides real time imaging of targeted area (e.g. retina) along with spatial targeted laser irradiation leading to targeted delivery of genes or other molecules. OCT based guided gene delivery was achieved by use of surface plasmon matched gold nanorods (GNRs) and low power CW laser which utilizes high light absorption properties of gold nanorods. The targeted delivery is achieved by surface modification of GNRs to target specific cell types. FIG. 9A shows a representative B-scan OCT image of wild type mouse retina at baseline. High power setting of the NIR laser beam (980 nm, 60 mW) was used to create pathological geographic atrophic region(s) of interest, as described in Example 2. FIG. 9B shows B-scan image of the retina immediately after OCT-guided laser irradiation, leading to detachment of retina (marked by arrow). In FIG. 9C, we show B-scan image of the retina 10 days after OCT-guided localized laser injury. The arrow points to thinning of retina (due to loss of photoreceptors) and hyperreflective RPE-Buch's membrane. FIG. 9D shows B-scan image of the retina 2 weeks after OCT-guided localized laser injury. Thinning of retina, hyperreflective RPE-Buch's membrane and fibrosis is visible. To sensitize the geographic atrophic regions of retina, optical delivery of therapeutic molecules to targeted regions of retina was carried out using the OCT-guided NIR laser microirradiation device, where real-time OCT imaging was conducted for obtaining feedback on retinal degeneration region. The arrow points to the injured retinal degeneration region, where nano-enhanced optical delivery (NOD) of Multi-Characteristic Opsin (MCO) plasmids was carried out at low power setting of the NIR laser (980 nm, 20 mW) beam. The region(s) of interest for optical delivery is(are) marked on the OCT image displayed on the viewing screen. FIG. 9E shows the OCT-guided targeted NOD of MCO-mCherry led to expression of reporter (mCherry, immunostained with green fluorescent secondary antibody) in the targeted region (marked by white rectangle). Cellular fluorescence is clearly visible in the targeted area as compared to non-targeted collateral areas of retina. To evaluate functional recovery in retinal regions after OCT-guided NIR laser gene delivery, micro-focal ERG measurements were carried out by OCT guided multi-color laser stimulation. FIG. 9F shows scotopic micro-focal ERG response obtained using blue (B), green (G) and red (R) light stimulation from a targeted photoreceptor damaged region (without NOD of MCO genes) showing diminished A and B-waves. OCT-guided targeted NOD of polychromatic opsin (MCO) led to improved blue/green/red stimulated focal ERG in the area injured by OCT-guided laser injury (FIG. 9G). Thus, OCT-guided laser gene delivery enabled recovery of functional deficits in the Dry-AMD mouse model created by OCT-guided laser injury, measured by micro-focal ERG.

Example 9C

Figure 9H:
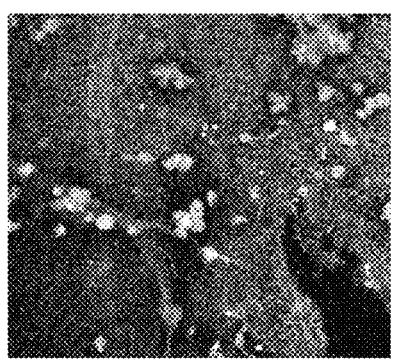
FIG. 9H. Spatially targeted OCT guided in-vivo laser-based nano-enhanced optical delivery (NOD) of large genes. NOD is achieved with near infrared (NIR) continuous wave (cw) laser beam by enhancing the laser intensity in the vicinity of targeted cells binding to functionalized gold nanorods with surface plasmon resonance peak matching the wavelength of the laser beam. Fluorescence image of transfected retina 1 week after OCT-guided 980 nm cw laser (10 mW) based nano-enhanced optical delivery (NOD) of large ABCA4-GFP genes, showing reporter (GFP) fluorescence (in green)
Figure 9I:
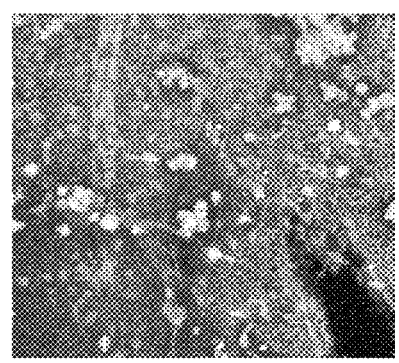
FIG. 9I. Overlay of nuclear stain (DAPI: Blue) and reporter (GFP) fluorescence image of the OCT-guided cw laser-based NOD of ABCA4-GFP plasmids.

The OCT-guided near-infrared laser irradiation device was used to for NOD of large (ABCA4-GFP) genes in retina. A mixture of CAG-ABCA4-eGFP plasmid along with functionalized gold nanorod solution (1 µl) was injected by a sterilized 29-gauge needle of a Hamilton micro-syringe inserted through the sclera into the vitreous cavity (intravitreal injection). FIG. 9H shows spatially targeted OCT guided in-vivo laser-(980 nm, 20 mW) microirradiation based nano-enhanced optical delivery (NOD) of large ABCA4 genes. NOD was achieved with near infrared (NIR) continuous wave (cw) laser beam by enhancing the laser intensity in the vicinity of targeted cells binding to functionalized gold nanorods with surface plasmon resonance peak matching the wavelength of the laser beam. Fluorescence image of transfected retina 1 week after OCT-guided 980 nm cw laser (10 mW) based nano-enhanced optical delivery (NOD) of large ABCA4-GFP genes, showing reporter (GFP) fluorescence (in green). FIG. 9I shows overlay of nuclear stain (DAPI: Blue) and reporter (GFP) fluorescence image of the OCT-guided cw laser-based NOD of ABCA4-GFP plasmids. During optical delivery, the OCT beam is kept turned ON so as to allow imaging of the region(s) of interests that provided feedback (about the eye movement) to the delivery laser beam delivery process so that the delivery laser beam scan could be readjusted to match the region of interest.

Figure 10:
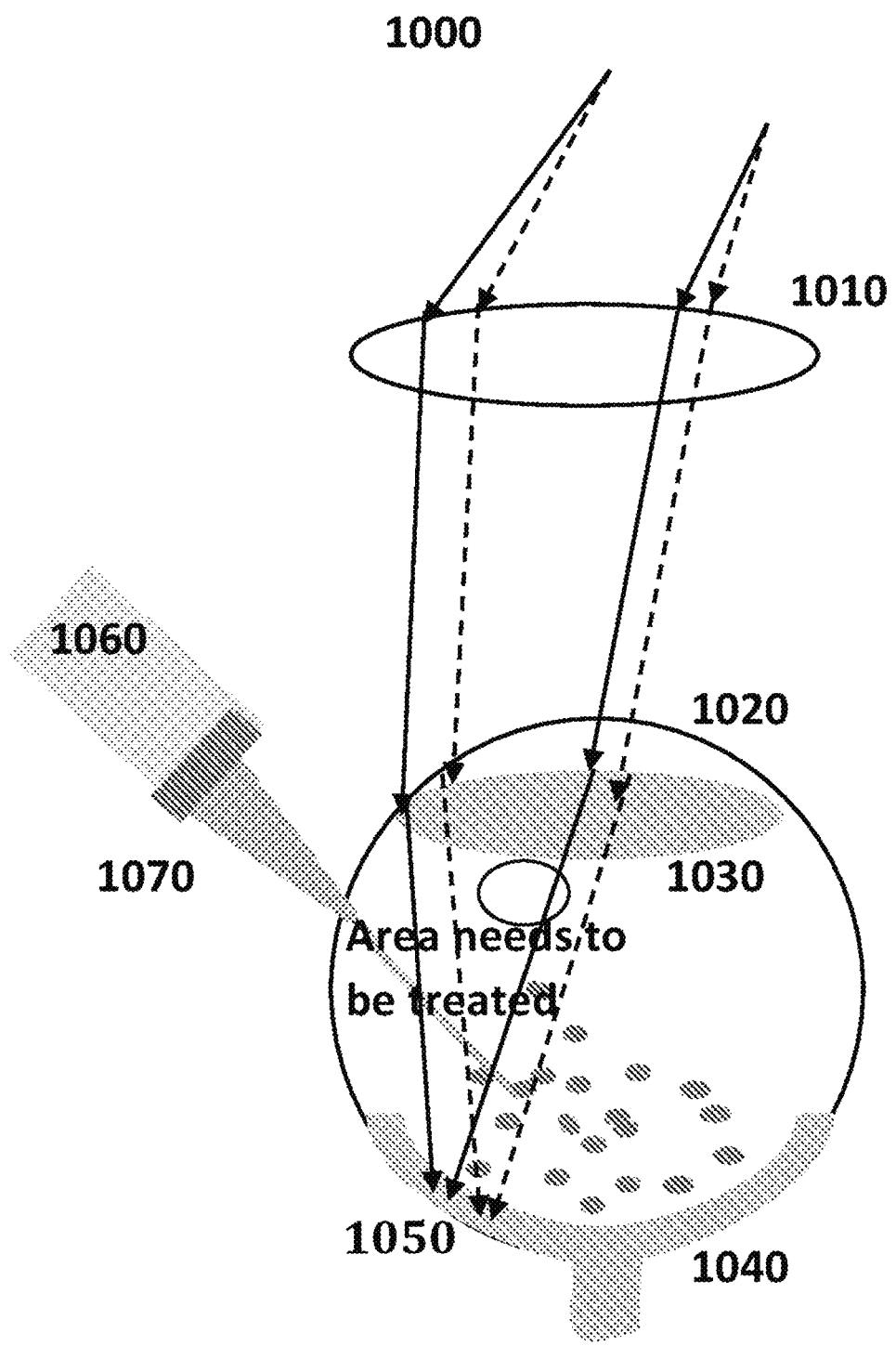
FIG. 10. Schematic of NOD-based controlled molecular delivery in targeted regions of retina. 1000: NIR laser for NOD; 1010: Optics for correcting beam distorted by cornea (1020) and lens (1030) to focus on retina (1040). 1050: Area needs to be treated; 1060: Gold nanorods and molecules to-be-injected; 1070: injector. The molecules (e.g., genes) injected into the vitreous through sclera. When a near-infrared (NIR) laser irradiates targeted regions of retina (circle), membrane of retinal cells bound with appropriate nano-rod(s) gets permeabilized for exogenous impermeable molecules (e.g. genes). The in-vivo gene delivery system consists of external optics for correcting beam propagation through cornea and lens in the eye to allow irradiation of spatially targeted regions of retina to be delivered with exogenous molecules.

FIG. 10 shows schematic process of NOD-based controlled molecular delivery in targeted regions of retina. The molecules (e.g., genes) injected into the vitreous through sclera. When a near-infrared (NIR) laser irradiates targeted regions of retina (circle), membrane of retinal cells bound with appropriate nano-rod(s) gets permeabilized for exogenous impermeable molecules (e.g. genes). The in-vivo gene delivery system consists of external optics (adaptive/scanning) for correcting beam propagation through cornea and lens in the eye to allow irradiation of spatially targeted regions of retina to be delivered with exogenous molecules. The gene delivery system is integrated with retina imaging modalities including Scanning laser Ophthalmoscopy, Optical Coherence Tomography and Fundoscopy.

Example 10

Nano-enhanced Optical Delivery using NIR laser beam was carried out with the in-vivo setup (FIG. 11A). Gold nano-rods (diameter: 10 nm, length: 40 nm) with surface Plasmon absorption maximum at 800 nm were used for NOD. The rd10 mice (N=6) were anesthetized with a mixture of ketamine (65 mg/kg), xylazine (7.5 mg/kg), and acepromazine (0.5 mg/kg). One drop of local anesthesia (0.5% proparacaine hydrochloride) was instilled into both the eyes of the animals. The functionalized gold nano-rods and 2 µl of opsin-mCherry plasmids (final concentration: 50 ng/µl) was injected into one of the eyes by a sterilized 32-G needle of a Hamilton micro-syringe inserted through the sclera into the vitreous cavity. As a negative control, the other eye was intravitreally injected with same volume of PBS. 1% Tropicamide ophthalmic solution was applied for dilating the pupil. The Pupil dilation can be seen the confocal laser scanning reflectance microscopic image (FIG. 11B). The cornea was kept moist with a balanced salt solution during the entire surgical procedure. The CW NIR laser beam exposure was varied. FIG. 11C shows the zoomed image of eye during the NOD laser exposure of the eye, injected with GNR and opsin plasmids. 5 weeks after injection of AAV-mGluR6-MCO-mCherry, the mice were sacrificed and retinal tissue was extracted. The confocal fluorescence image (FIG. 11D) shows expression of opsin-mCherry in the retinal cells. The retina of PBS-injected control eye does not show any characteristic (mCherry) fluorescence. Further, the peripheral retina (without NIR laser irradiation) served as internal negative control.

While NOD method successfully demonstrated targeted gene delivery into mice retina, successful delivery of therapeutic genes in humans, having thick inner limiting membrane (ILM) (96), may require use of chemical agent (e.g. AAA) that can transiently permeabilize the inner limiting membrane of the human eye.

Example 11

Figure 12:
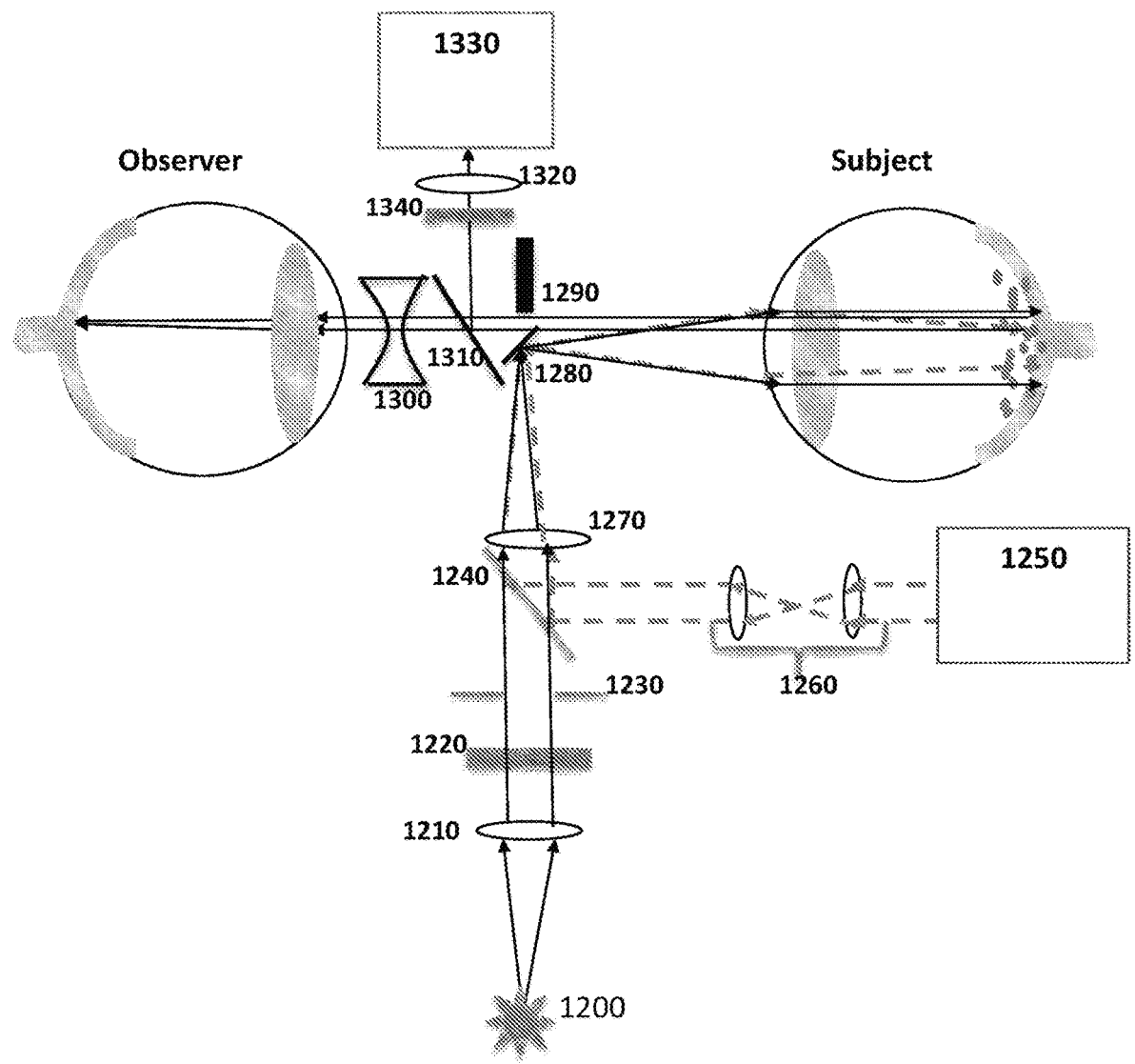
FIG. 12. Schematic of the integrated device for NOD and imaging ophthalmoscope for fluorescence and/or normal fundoscopy. 1200: Visible Light source (LED/lamp/laser); 1210: Lens-1; 1220: excitation band pass filter; 1230: aperture; 1240: Dichroic mirror; 1250 NIR laser and controller; 1260: Beam divergence and expansion controller; 1270: Lens-2; 1280: mirror-1; 1290: hole; 1300: compensation lens; 1310: mirror-2; 1320: Lens-3; 1330: Camera and display; 1340: emission band pass filter.

For use of NOD in eye of human subjects, an integrated system comprising of NIR laser for NOD and target retina examination by slit lamp Ophthalmoscope/fundoscopy is presented. FIG. 12 shows a Schematic diagram of the integrated device for NOD and imaging ophthalmoscope for fluorescence and/or normal fundoscopy. Light emitted from 1200 (a visible light source such as LED, lamp or laser) is expanded/collimated/focused using lenses (1210), transmitted through the aperture (1220) and directed to the retina by mirror 1 (1280). The excitation band pass filter (1220) is optionally used for selecting excitation band in case of fluorescence examination of the retina. The near-infrared NOD laser (1250) beam is expanded by a beam divergence and expansion controller (1260) and directed to the subject's eye by use of the dichroic mirror (1240), lens (1270) and mirror 1 (1280). Light reflected (or fluorescence) from the retina is collected by a combination of mirror 2 (1310), lens 3 (1320) and optionally through an emission filter (1340). The compensation lens (1300) is used by the observer to visualize the subject's retina. After identifying the pathological areas, the subject's eye(s) will be injected with GNR and therapeutic molecules. The observer-operator will then target the NIR laser beam to the pathological areas and will expose those areas to clinically/pre-clinically tested doses (i.e., power and exposure time) within safety limit.

Example 12

Figure 13:
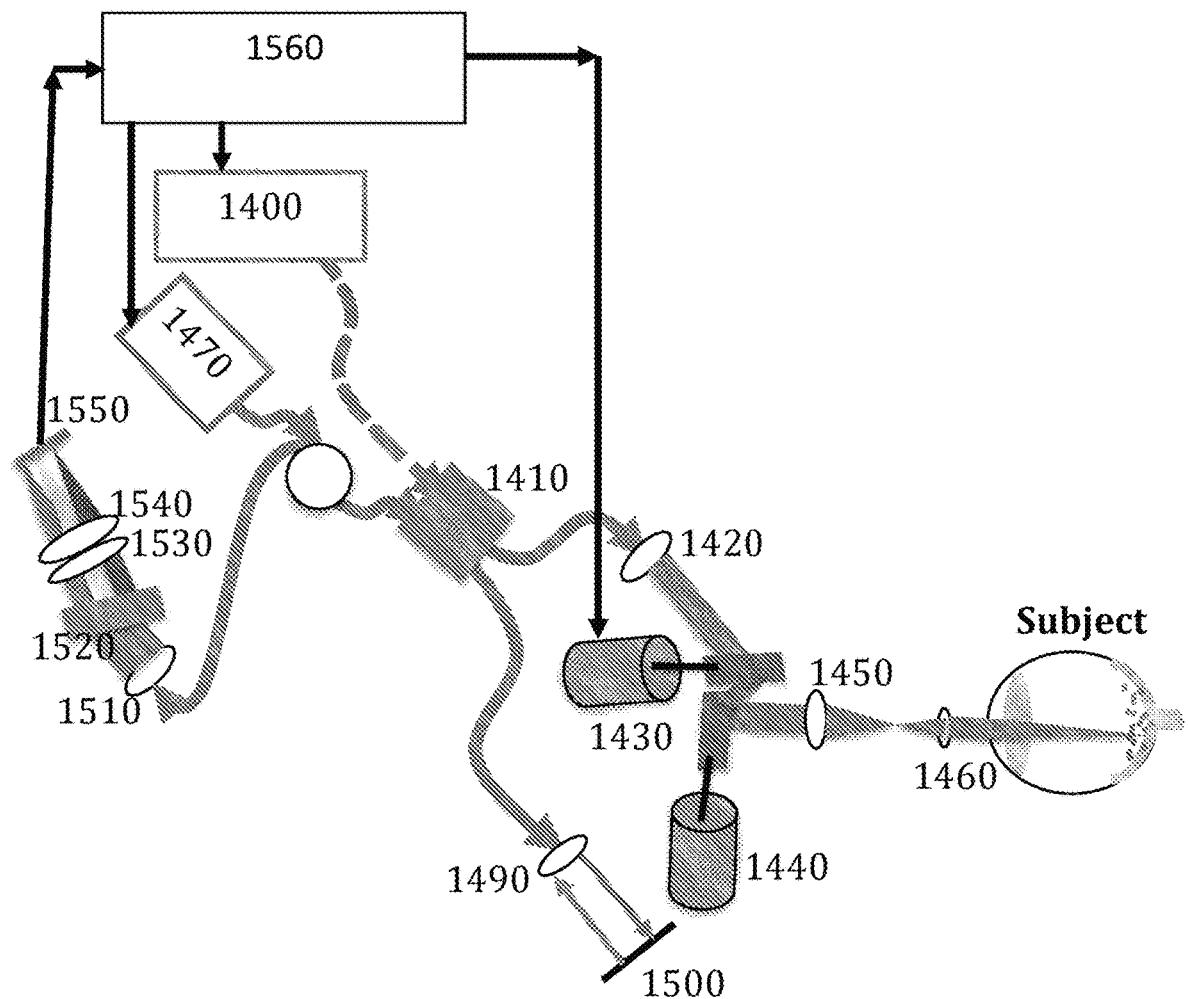
FIG. 13. Schematic of integrated device for NOD and imaging by OCT. 1400: NIR laser; 1410: Fiber coupler; 1420: collimating lens-1; 1430, 1440: scanning mirrors; 1450, 1460: Lens pair; 1470: low coherence source; 1480: Circulator; 1490: collimating lens-2; 1500: reference mirror; 1510: collimating lens-3; 1520: grating; 1530, 1540: lens pair; 1550: camera; 1560: Computer, display and controller.

Further, for use of NOD in eye of human subjects, an integrated system comprising of NIR laser for NOD with device for obtaining feedback by optical coherence tomography (OCT) is presented. FIG. 13 shows a schematic setup of integrated device for NOD (1400) and feedback imaging by OCT. The OCT system consists of a NIR low coherence source (1470) which is routed through a Circulator (1480) into a 2×2 Fiber coupler (1410). The NIR laser (1400) for NOD, selected to have a wavelength spectrally separated from that of the OCT source, is coupled to the second input channel of the fiber coupler (1410). The NOD laser beam emanating from the out put of the fiber coupler is collimated by a collimating lens (1420) and targeted to selected retinal areas by scanning mirrors (1430, 1440) and pair of telescopic lenses (1450, 1460). During identification of retinal pathology, the NIR laser beam for NOD is switched off. The beam from the low-coherence source (for OCT), at the output end of FC is collimated by the same collimating lens (1420) and scanned by the pair of mirrors (1430, 1440). The OCT beam is delivered to the eye by use of telescopic lenses (1450, 1460). The reference beam emanating from the other port of the fiber coupler is collimated by another collimating lens (1490) and reflected back via the same port by use of reference mirror (1500) as shown in FIG. 13. The back-reflected sample beam from the eye (and retina) and the reference beam are routed back via the circulator (1480) to a spectrometer, which comprises of grating (1520) and lenses (1530, 1540). The interferogram is recorded in a camera (1550) and processed to obtain structural information of the eye and retina in particular, indicating its pathological condition. The regions of interest for NOD will be marked on the image displayed on the viewing screen (1560).

After identifying the pathological areas that need treatment, the subject's eye(s) will be injected with GNR and therapeutic molecules into the vitreous cavity or sub-retinal space depending on the targeted retinal layer. The NIR laser beam will be switched ON and targeted to the pathological region(s) of interest. These areas will be exposed to clinically tested NIR laser doses (i.e., power and exposure time) for efficient and minimally invasive delivery of therapeutic molecules.

During Nano-enhanced optical delivery, the OCT beam is kept turned ON so as to allow imaging of the region(s) of interests that will provide feedback (about the eye movement) to the NOD laser beam delivery process so that the NOD laser beam scan can be dynamically readjusted to match the region(s) of interest. Though NOD integrated with Spectral Domain OCT has been presented here, the invention does not exclude use of other OCT modalities for identifying retinal pathologies and providing feedback to the NOD laser beam delivery.

Example 13

Figure 14:
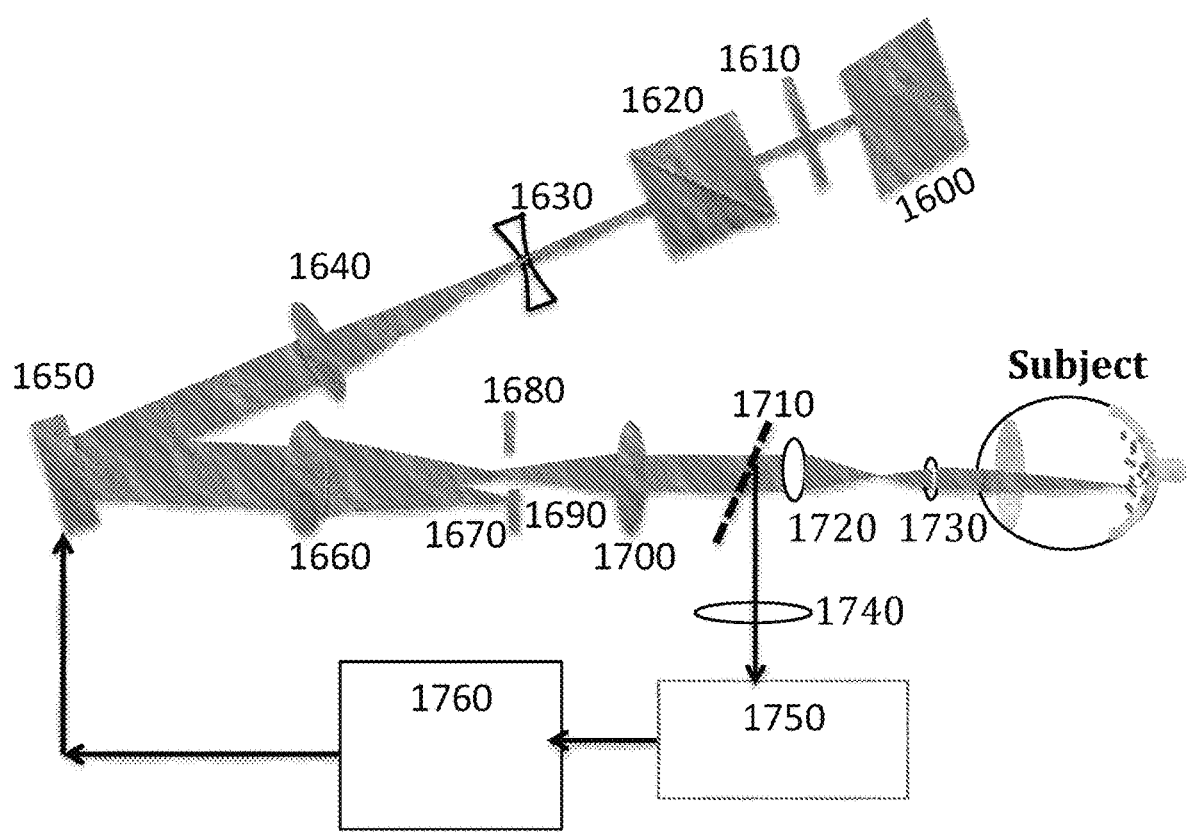
FIG. 14. Schematic setup for shaping laser beam for NOD by DMD/SLM to geographic atrophies with feedback imaging by OCT/Fundoscopy. 1600: NIR laser; 1610: half wave plate; 1620: polarizer; 1630: lens-1; 1640: lens-2; 1650: spatial light modulator or Digital micro-mirror device; 1660: lens-3; 1670: un-deviated beam; 1680: pin hole; 1690: modulated beam; 1700: lens-4; 1710: dichroic mirror; 1720: Lens-5; 1730: Lens-6; 1740: Lens-7; 1750: OCT or fundoscope; 1760: Computer and display.

In case of rapid movement of organ (e.g. eye), it may be advantageous to use a spatially sculpted NIR beam to match the shape of the region(s) of interest in the tissue requiring targeted molecular delivery by NOD. FIG. 14 depicts schematic of a setup for shaping the NIR laser beam for NOD by DMD/SLM to fit the targeted regions (e.g., geographic atrophies of retina in degenerative diseases) so that the therapeutic molecules (e.g. genes) can be delivered in a high throughput manner. In this method, feedback imaging by OCT or Fundoscopy can be obtained to ensure exact matching of the NOD laser beam to the targeted areas. After identifying the pathological areas, the subject's eye(s) is(are) injected with GNR and therapeutic molecules. For controlling the power and/or polarization of the NIR laser beam (1600) used for NOD, the beam is transmitted through half wave plate (1610) and polarizer (1620). The beam is expanded and collimated by lenses (1630, 1640), which illuminates a spatial light modulator or Digital micro-mirror device (1650). The 1650 is programmed to modulate the laser beam shape (based on feedback by OCT or fundoscopy) so as to match the regions of tissues requiring NOD laser molecular delivery. The un-deviated beam (1670) from the 1650 is blocked by a lens (1660) pinhole (1680) assembly. The spatially modulated beam (1690) is transmitted through the 1680, collimated by a lens (1700) and transmitted through the dichroic mirror (1710) to the telescopic lens pair (1720, 1730) that delivers the beam to the tissue (e.g. retina). The pathological area(s) is (are) exposed to the clinically/pre-clinically tested doses (i.e., power and exposure time) of NIR laser beam within safety limit.

Example 14

Figure 15:
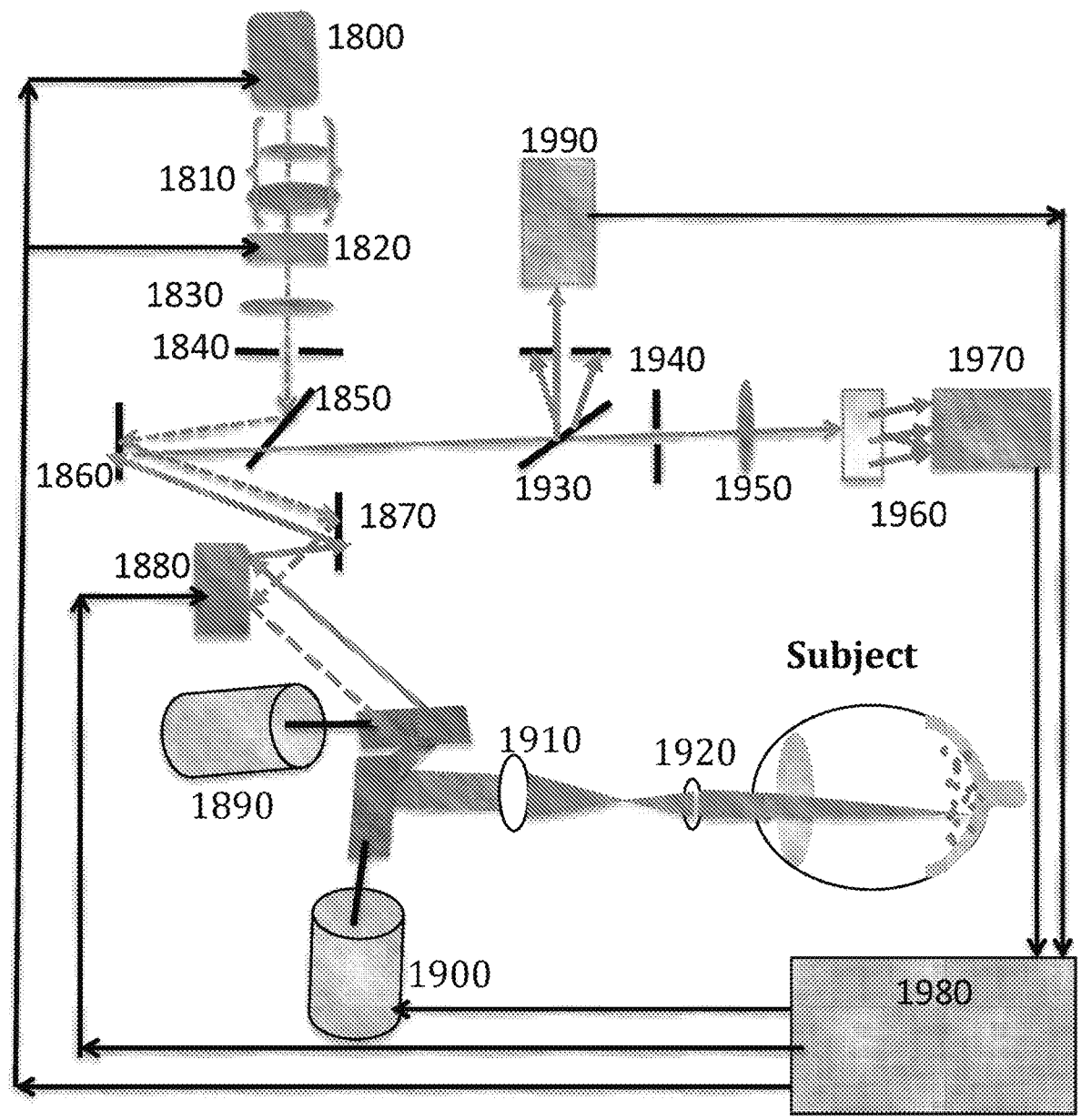
FIG. 15. Schematic of adaptive optics setup for correcting laser beam for NOD to geographic atrophy areas of retina. 1800: NOD/imaging laser; 1810: beam expander/collimator; 1820: beam controller (polarization/power/exposure); 1830: lens-1; 1840: pin hole 1; 1850: dichroic mirror; 1860: mirror-1; 1870: mirror-2; 1880: Adaptive optics mirror; 1890: scanning mirror-1; 1900: scanning mirror-2; 1910: lens-2; 1920: lens-3; 1930: beam splitter; 1940: pin hole 2; 1950: lens-4; 1960: wave front sensor; 1970: camera; 1980: computer and controller; 1990: photo-detector.

In addition to motion artifacts, challenges in perfectly matching the margins of the NIR laser for NOD may arise due to scattering tissue and imperfect optical media of the eye. To correct for wave front distortions in NOD laser beam (1800), use of adaptive optics is presented as shown in FIG. 15. This is to improve the performance of the NOD process. This is accomplished by compensating for the higher order aberrations originating from the cornea and the lens of the eye by using deformable adaptive optic mirror (1880). FIG. 15 shows a schematic of the setup utilizing adaptive optics for correcting the laser beam for nano-enhanced optical delivery of molecules to cells in the geographic atrophy areas of retina. The NOD laser beam (1800) is expanded and collimated by a beam expander (1810). The beam controller (1820) controls the polarization, power and exposure of the NOD laser beam. The beam after passing through lens (1830) and pinhole (1840) is reflected by a dichroic mirror 1 (1850) to folding mirrors (1860, 1870) that directs the beam to the deformable adaptive optic mirror (1880). First the NOD laser beam is operated in low power mode to initialize the 1880.

The beam is maneuvered by pair of scanning mirrors (1890, 1900), which sends the beam (dotted arrows) to retina via the telescope lens pair (1910, 1920). The back-reflected beam from eye with distorted wave front (solid arrows) traverses via the dichroic mirror 1 (1850) to the beam splitter (1930). The reflected part of the beam (from 1930) passes through a pinhole (1940) to a photo-detector (1990) to enable ocular imaging (similar to scanning laser ophthalmoscope). The transmitted beam (through 1930) passes through a pinhole and lens (1950) to a wave front sensor (1960) such as Shack-Hartmann's. The wave front distortion mapped in near-real time is used to control the 1880 so as to compensate for the distortions in the NOD laser beam at operational conditions. After identifying the pathological areas, the subject's eye(s) is injected with GNR and therapeutic molecules. Then irradiation of the spatially targeted regions of retina is carried out by wave front corrected NIR laser beam at clinically/pre-clinically tested doses (i.e., power and exposure time) within safety limit.

For optogenetic vision restoration, patient-to-patient variability and time-dependent changes in spatial-distribution of retinal-degeneration demands site-specific expression of the opsin. For example, spatially targeted delivery of opsin-encoding gene is required in macula, which loses photosensitivity due to loss of photoreceptors in case of dry-AMD (97-99). With viral or other non-viral (e.g. electroporation, lipofection) method, the opsin constructs will be delivered everywhere, causing un-controlled expression over the whole retina. This will cause complications in functioning of non-degenerated areas of retina (100) by interference of light-evoked activities in multiple layers of the retinal circuitry. Therefore, application of spatially targeted NOD of opsins in degenerated retina will allow photo-stimulation of retinal cells in the areas of photoreceptor-degeneration, leading to vision restoration.

The invention provides a method of improving or restoring vision, comprising administering to a subject to the compositions described herein. Compositions of the mixture solution to be injected intravitreally or sub-retinal for vision restoration by the invented NOD method includes: (i) opsin plasmids, (ii) functionalized gold nano-rods and (iii) adjunctive for stabilization of molecules, or minimization of damage, or enhancement of their binding or mobility. For example, invention delivery is improvised by use of optimized formulation of Alpha-aminoadipic acid (AAA, a structural analogue of glutamate which is known to reversibly disturb the ILM (101, 102)) together with opsin-plasmid and GNRs to transiently permeabilize inner limiting membrane of human eye. Further, to allow promoter-specific expression of MCO in RGCs or bipolar cells, suitable promoter (i.e. γ-synuclein for RGC and mGluR6 for bipolar) is used upstream of opsin plasmid.

Surgical risks of existing complex retinal-implantation procedures for improving vision are very high. This is especially more of a concern in case of replacement of the implant due to device-failure during chronic usage. Further in diseases such as RP and dry-AMD, degeneration of retina advances at 2 mm<2>per year. During such progressive loss, the NOD process can be easily repeated allowing opsin expression in new degenerated retinal area(s). Our proposed method of expression of opsin is easy-to-adapt into current clinical practice: (i) Intravitreal/sub-retinal injection and incubation of the functionalized gold nano-rods; (ii) Intravitreal/sub-retinal injection of opsin encoding plasmids; and (iii) Targeted NOD of opsin-plasmids into retinal cells in the degenerated areas based on imaging feedback.

NIR light beam (used for NOD) has practically negligible absorption coefficient in most of the tissues and transparent ocular layers such as the cornea, lens, and neural retina. Further, water absorption at near-infrared (800-900 nm) nm (NOD laser beam) is minimal. However, the cw NIR light (used for NOD) may get absorbed by the retinal pigment epithelium. To minimize temperature rise (which may elicit damage to tissue), the NOD laser beam can be pulsated and the duty cycle is varied to achieve optimal effect (i.e. maximum delivery in retinal tissue without perturbing the retinal pigment epithelium).

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the device, compositions and methods of this invention have been described in terms of preferred embodiments, it will be apparent to those of skill in the art that variations may be applied to the device, compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

As used in this document, both in the description and in the claims, and as customarily used in the art, the words "substantially," "approximately," and similar terms of approximation are used to account for measuring and manufacturing tolerances, manufacturing variations, and measuring and manufacturing imprecisions that are inescapable parts of fabricating any mechanism, structure, or composition in the physical world.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. The purpose of the abstract of this document is to enable the U.S. Patent and Trademark Office, as well as readers who are not familiar with patent or legal terms or phraseology, to determine quickly from a cursory inspection the nature of the technical disclosure of the application. The abstract is not intended to define the invention, nor is it intended to limit to the scope of the invention. Therefore, the invention is not to be restricted or limited except in accordance with the following claims and their legal equivalents.

REFERENCES

The following references, to the extent that they provide exemplary procedural or other details supplementary to those set forth above, are specifically incorporated by reference.

1 Waheed, N. K., Moult, E. M., Fujimoto, J. G. & Rosenfeld, P. J. Optical Coherence Tomography Angiography of Dry Age-Related Macular Degeneration. *Dev Ophthalmol* 56, 91-100, doi:10.1159/000442784 (2016).

2 Hee, M. R. et al. Optical coherence tomography of macular holes. *Ophthalmology* 102, 748-756 (1995).

3 Hee, M. R. et al. Optical coherence tomography of the human retina. *Arch Ophthalmol* 113, 325-332 (1995).

4 Swanson, E. A. et al. In vivo retinal imaging by optical coherence tomography. *Opt Lett* 18, 1864-1866 (1993).

What is claimed is:

1. A device comprising:
   a. a laser irradiation sub-assembly configured to generate a laser beam for irradiation of a sample comprising at least one of living tissue, neurons, retina cells, brain cells, heart cells, muscle cells, epithelial cells, endothelial cells, blood and skin cells;
   b. a visible light source combinable with the laser beam by a beam combiner and configured to at least one of:
      locate the laser beam;
      stimulate the sample; and
      fixate the sample;
   c. an imaging light source sub-assembly which emits a light beam with a selected wavelength in a range from 400 nm to 1600 nm, wherein the selected wavelength is not perturbative to the functioning or structure of the sample;
   d. wherein the light beam emitted from the imaging light source sub-assembly is combinable with the laser beam and able to be split by a beam splitter to generate a split combined beam having a first part and second part;
   e. wherein the first part of the split combined beam is guided via an optical system comprising at least one mirror, at least one focusing element and at least one lens to irradiate the sample;
   f. wherein the at least one mirror and at least one focusing element is actuatable to control the position and size of an irradiation spot on the sample;
   g. wherein back-scattered light from the sample is able to pass through the optical system and the beam splitter to a detector;
   h. wherein the second part of the split combined beam is able to traverse through an optical sub-assembly comprising a reference arm;
   i. wherein optionally, back-reflected light from the reference arm is able to pass through the beam splitter to the detector to interfere with the back-scattered light from the sample;
   j. wherein a signal from the detector is processed to obtain at least one of:
      a depth-resolved image of the sample;

measurements of physical properties of the sample; and measurements of physiological properties of the sample;
k. wherein a laser beam irradiation dose and pattern in a targeted region is controllable for performing at least one of ablation, stimulation, molecular delivery and alteration of the sample; and
l. wherein a dose and pattern of the light beam from the visible light source is controllable and able to be synchronized with the imaging light source for mapping functional properties of the sample.

2. The device according to claim 1, wherein an average laser beam power at a sample plane is up to 1 Watt.

3. The device according to claim 1, wherein a wavelength of the laser beam ranges from 300 nm to 2200 nm.

4. The device according to claim 1, wherein the laser beam comprises pulses ranging from femtoseconds to seconds.

5. The device according to claim 1, wherein the visible light source is operable to emit light with a wavelength ranging from 400 to 700 nm and a power at a sample plane up to 10 mW.

6. The device according to claim 1, wherein an imaging light power at a sample plane is below 10 mW.

7. The device according to claim 1, wherein the beam combiner and beam splitter are based on any one of: a fiber-optic beam splitter, a wavelength division multiplexor, or a free-space optics, which is optimized for polarization and wavelength of the laser or light beam.

8. The device according to claim 1, wherein the back-scattered light from the sample is elastically scattered light or inelastically scattered light, and measurable by a band pass or high pass optical filter.

9. The device according to claim 1, wherein the detector is selected from at least one of a single photodetector, a linear array of photodetectors, a photo-multiplier tube, a camera, and a spectrometer.

10. The device according to claim 1, wherein physical properties include reflectivity, changes in refractive index, temperature, topography and thickness of layer(s);
   a. wherein the reflectivity is measured from the intensity of image(s) of a sample layer(s) at different depth(s) acquired from the back-scattered light from the sample;
   b. wherein the changes in refractive index is estimated from the optical path difference measured by the interference of the imaging light beam backscattered from the sample with a reference beam;
   c. wherein the temperature is calculated from the changes in the optical path difference;
   d. wherein the topography and thickness of different layers is measured from the depth-resolved image(s) of the sample.

11. The device according to claim 1, wherein monitoring of physiological properties comprises analyzing the electrical response of the sample measured by electrode(s) with or without stimulation by the light from the visible light source, or by analyzing the properties comprising intensity, phase and fluorescence of back-scattered sample beam measured by the detector.

12. The device according to claim 1, wherein the laser beam irradiation is capable of performing selective ablation by absorption of the targeted sample or dielectric breakdown of the sample in focused volume.

13. The device according to claim 1 for use in the treatment of glaucoma, retinal dystrophy or for use in blood vessel removal from skin and eyes.

14. The device according to claim 1, wherein the laser beam irradiation is capable of perforating the sample to allow delivery of impermeable molecules comprising at least one of drugs, proteins, and nucleic acids.

15. The device according to claim 1, wherein the laser beam irradiation is capable of stimulation of the sample by electronic excitation of specific molecules of the sample or increasing temperature of the sample.

16. The device according to claim 1, wherein the visible light source is configured to stimulate the sample by electronic excitation of specific molecules of the sample for probing the functioning of the sample or therapeutic use.

17. The device according to claim 1, wherein the laser beam is integrated with a slit lamp or scanning laser Ophthalmoscope for fundoscopy of a subject's eye to identify region(s) of interest in a retina that requires Nano-enhanced Optical Delivery (NOD) by use of light-enhancing nanoparticles.

18. The device according to claim 17, wherein the laser beam is integrated with optical coherence tomography for identifying retinal pathologies and providing feedback to the NOD laser beam delivery.

19. The device according to claim 17, wherein an NIR laser for NOD is spatially sculpted by spatial light modulator or digital micro-mirror device to enhance throughput and match the shape(s) of the region(s) of interest in the tissue of a moving organ requiring targeted molecular delivery by NOD.

20. The device according to claim 17, wherein a wave front of an NIR laser beam for NOD is corrected to account for distortions arising due to scattering properties of target tissue and imperfect optical media of the eye.

21. The device according to claim 17, wherein NOD is improvised by use of adjunctive for stabilization of to-be-injected molecules, or enhancement of their binding or mobility, permeability of inner limiting membrane, or minimization of cellular damage.

* * * * *